US011542392B1

(12) United States Patent
Multari

(10) Patent No.: US 11,542,392 B1
(45) Date of Patent: Jan. 3, 2023

(54) MULTIFUNCTIONAL PARTICLE ADDITIVE FOR ENHANCEMENT OF TOUGHNESS AND DEGRADATION IN BIODEGRADABLE POLYMERS

(71) Applicant: TRUCAPSOL LLC, Bethlehem, PA (US)

(72) Inventor: Caroline Multari, Bethlehem, PA (US)

(73) Assignee: TRUCAPSOL LLC, Bethlehem, PA (US)

( * ) Notice: Subject to any disclaimer, the term of this patent is extended or adjusted under 35 U.S.C. 154(b) by 414 days.

(21) Appl. No.: 16/853,003

(22) Filed: Apr. 20, 2020

Related U.S. Application Data

(60) Provisional application No. 62/836,062, filed on Apr. 18, 2019.

(51) Int. Cl.
C08L 67/04 (2006.01)
B01J 13/14 (2006.01)
C08J 3/20 (2006.01)

(52) U.S. Cl.
CPC ............ C08L 67/04 (2013.01); B01J 13/14 (2013.01); C08J 3/201 (2013.01); C08J 2367/04 (2013.01); C08L 2201/06 (2013.01)

(58) Field of Classification Search
CPC ....... C08L 67/04; C08L 2201/06; B01J 13/14; C08J 3/201; C08J 2367/04
USPC ......................................................... 504/359
See application file for complete search history.

(56) References Cited

U.S. PATENT DOCUMENTS

| | | |
|---|---|---|
| 3,345,358 A | 10/1967 | Inklaar |
| 3,819,838 A | 6/1974 | Smith et al. |
| 3,870,542 A | 3/1975 | Ida et al. |
| 3,900,492 A | 8/1975 | Buckler et al. |
| 4,626,471 A | 12/1986 | Chao |
| 5,227,446 A | 7/1993 | Denzinger et al. |
| 5,550,189 A | 8/1996 | Qin et al. |
| 5,574,179 A | 11/1996 | Wahl et al. |
| 5,601,760 A | 2/1997 | Rosenberg |
| 5,837,747 A | 11/1998 | Soon-Shiong et al. |
| 6,248,909 B1 | 6/2001 | Akimoto et al. |
| 6,465,016 B2 | 10/2002 | Parikh et al. |
| 6,572,919 B2 | 6/2003 | Westland et al. |
| 6,596,073 B1 | 7/2003 | Nyssen et al. |
| 6,855,335 B2 | 2/2005 | Seok et al. |
| 7,431,986 B2 | 10/2008 | Van Lengerich et al. |
| 8,900,495 B2 | 12/2014 | Pacorel et al. |
| 9,205,395 B2 | 12/2015 | Yan |
| 9,332,774 B2 | 5/2016 | Nakhasi et al. |
| 9,427,719 B2 | 8/2016 | Viaud-Massuard et al. |
| 9,714,397 B2 | 7/2017 | Feng et al. |
| 9,937,477 B2 | 4/2018 | Zhang et al. |
| 9,944,886 B2 | 4/2018 | Hitchcock et al. |
| 9,993,401 B2 | 6/2018 | Barnett et al. |
| 10,188,593 B2 | 1/2019 | Dihora et al. |
| 11,179,302 B2 | 11/2021 | Dardelle |
| 11,344,502 B1 | 5/2022 | Dihora et al. |
| 2004/0017017 A1 | 1/2004 | Van Lengerich et al. |
| 2004/0033264 A1 | 2/2004 | Sawhney |
| 2005/0272628 A1 | 12/2005 | Meli et al. |
| 2005/0276831 A1 | 12/2005 | Dihora et al. |
| 2008/0085297 A1* | 4/2008 | Dave ....................... A61L 31/06 977/906 |
| 2008/0103265 A1 | 5/2008 | Schocker et al. |
| 2008/0167188 A1 | 7/2008 | Fischer et al. |
| 2009/0209661 A1 | 8/2009 | Somerville Roberts et al. |
| 2010/0011610 A1 | 1/2010 | Bittorf et al. |
| 2010/0028451 A1 | 2/2010 | Kaplan et al. |
| 2011/0052680 A1 | 3/2011 | Hendrickson et al. |
| 2011/0268778 A1 | 11/2011 | Dihora et al. |
| 2011/0268802 A1 | 11/2011 | Dihora et al. |
| 2012/0128752 A1 | 5/2012 | Loo et al. |
| 2013/0004617 A1 | 1/2013 | Zhang et al. |
| 2013/0022654 A1 | 1/2013 | Deshmukh et al. |
| 2013/0084379 A1 | 4/2013 | Gregson et al. |
| 2013/0239429 A1 | 9/2013 | Vella et al. |
| 2014/0199244 A1 | 7/2014 | Rijcken et al. |

(Continued)

FOREIGN PATENT DOCUMENTS

| | | |
|---|---|---|
| CA | 1049335 A | 2/1979 |
| EP | 0815743 A2 | 1/1998 |

(Continued)

OTHER PUBLICATIONS

Adhesives Magazine (2016). Sartomer: Acrylate Oliogmer. Available at: https://www.adhesivesmag.com/articles/94922-sartomer-acrylate-oligomer.
Leung et al. (2017). Enteric coating of micron-size drug particles through a Würster fluid-bed process. Powder Technology, 317, 247-252.
Silverajah et al. (2012). Mechanical, thermal and morphological properties of poly (lactic acid)/epoxidized palm olein blend. Molecules, 17(10), 11729-11747.
Tmakova et al. (2015). Plant-derived surfactants as an alternative to synthetic surfactants: surface and antioxidant activities. Chemical Papers, 70(2), 188-196.

(Continued)

Primary Examiner — Hui H Chin
(74) Attorney, Agent, or Firm — Caesar Rivise, PC

(57) ABSTRACT

Disclosed is a biodegradable resin composite material including a biodegradable polymer resin and multifunctional particles, wherein: (a) the multifunctional particles include 10-70 wt. % of a hydrophobic active ingredient, 21-72 wt. % of a polysaccharide, 3.80-20 wt. % of a crosslinking agent, 1.00-6 wt. % of a catalyst, 0.10-5 wt. % of a silica flow aid, optionally 0.10-5 wt. % of a desiccant, optionally 0.20-20 wt. % emulsifier, optionally 1-10 wt. % of a degradation enhancer, and optionally 1-10 wt. % of particle dispersion aids; (b) the multifunctional particles are anhydrous; and (c) the hydrophobic active ingredient is encapsulated in a crosslinked polysaccharide matrix. Alternative multifunctional particles useful in the invention are also disclosed.

16 Claims, 4 Drawing Sheets

(56) References Cited

U.S. PATENT DOCUMENTS

| | | |
|---|---|---|
| 2014/0335032 A1 | 11/2014 | Panandiker et al. |
| 2015/0252312 A1 | 9/2015 | de Villeneuve et al. |
| 2016/0038428 A1 | 2/2016 | Harel et al. |
| 2016/0128944 A1 | 5/2016 | Chawrai et al. |
| 2016/0158121 A1 | 6/2016 | Lei et al. |
| 2016/0166480 A1 | 6/2016 | Lei et al. |
| 2016/0206561 A1 | 7/2016 | Kohane et al. |
| 2016/0228338 A9 | 8/2016 | Dihora et al. |
| 2017/0165627 A1 | 6/2017 | Duan et al. |
| 2017/0360676 A1* | 12/2017 | Dihora ............ C11D 3/001 |
| 2018/0015009 A1 | 1/2018 | Soubiran et al. |
| 2018/0042825 A1 | 2/2018 | Lei et al. |
| 2019/0275490 A1 | 9/2019 | Bachawala |
| 2021/0045409 A1 | 2/2021 | Witteveen et al. |
| 2022/0133603 A1 | 5/2022 | Bachawala et al. |

FOREIGN PATENT DOCUMENTS

| | | |
|---|---|---|
| EP | 1371410 A1 | 12/2003 |
| EP | 1797946 A2 | 6/2007 |
| WO | 9901214 A1 | 1/1999 |
| WO | 0105926 A1 | 1/2001 |
| WO | 03013538 A1 | 2/2003 |
| WO | 2004064971 A2 | 8/2004 |
| WO | 2006024411 A2 | 3/2006 |
| WO | 2007135583 A2 | 11/2007 |
| WO | 2008118133 A2 | 10/2008 |
| WO | 2009098226 A1 | 8/2009 |
| WO | 2011041395 A2 | 4/2011 |
| WO | 2015091877 A1 | 6/2015 |
| WO | 2016071151 A1 | 5/2016 |
| WO | 2017023830 A1 | 2/2017 |
| WO | 2020195132 A1 | 10/2020 |

OTHER PUBLICATIONS

Werner et al. (2007). Air-suspension particle coating in the food industry: Part I—State of the art. Powder Technology, 171(1), 25-33.
English language abstract for WO 2009098226 A1 (2009).
English language abstract for WO 2020195132 A1 (2020).
http://polymerdatabase.com/polymer%20physics/sigma.html downloaded on Apr. 29, 2022.
Ko et al., "Characterization of hydrophilic-hydrophobic polymeric surfaces by contact angle measurements", Journal of Colloid and Interface Science, vol. 82(1) (1981).
OECD 301D method (OECD 1992, Test No. 301 Ready Biodegradability, OECD Guidelines for the Testing of Chemicals, Section 3, OECD Publishing, Paris, https://doi.org/10.1787/9789264070349-en.
Thakore et al. (2001). "Studies on biodegradability, morphology and thermo-mechanical properties of LDPE/modified starch blends." European polymer journal, 37(1), 151-160.
Luo et al., "Zein-Based Micro- and Nano-Particles for Drug and Nutrient Delivery: A Review", J. Appl. Polym. Sci., vol. 40696, 12 pages (2014).
International Search Report for PCT/US2017/037855, dated Nov. 2, 2017.
International Search Report for PCT/US2019/018959, dated Jul. 8, 2019.

* cited by examiner

Fig. 6A     Fig. 6B     Fig. 6C
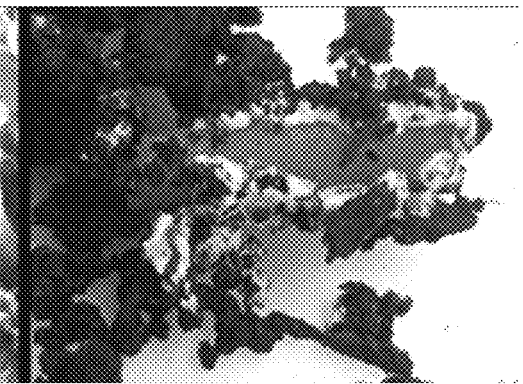
Fig. 7
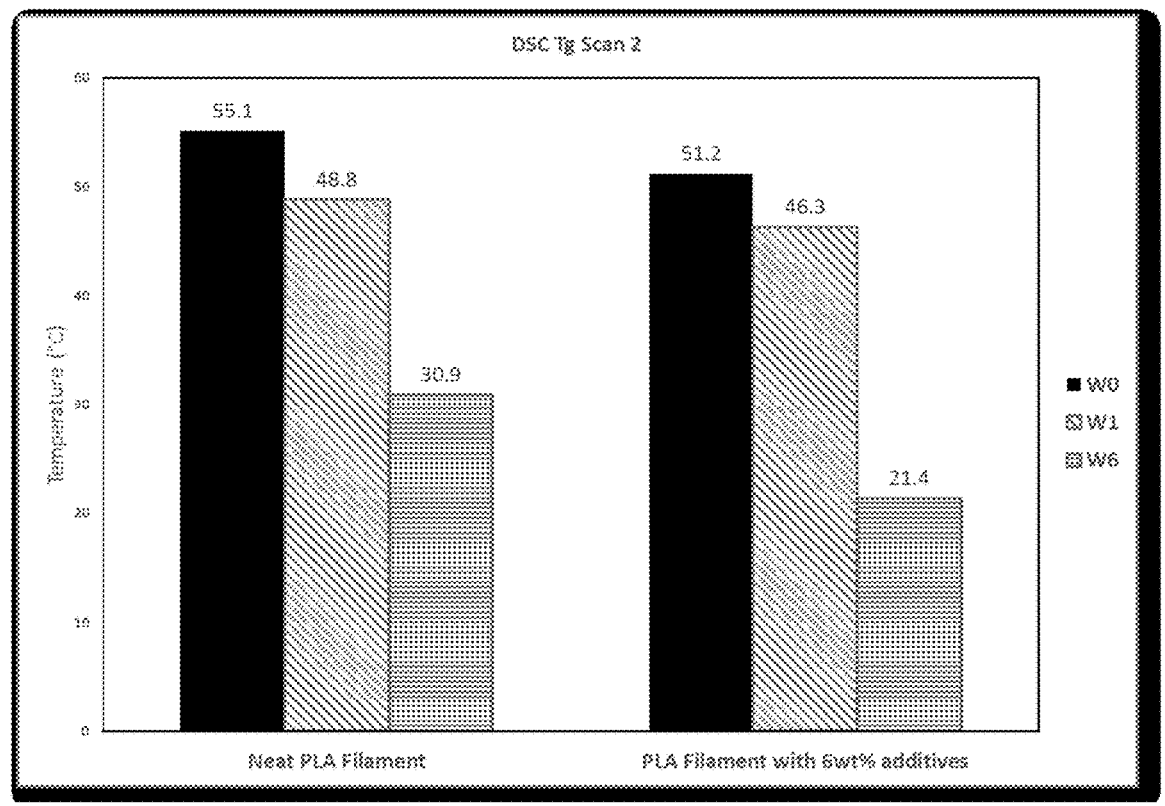

MULTIFUNCTIONAL PARTICLE ADDITIVE FOR ENHANCEMENT OF TOUGHNESS AND DEGRADATION IN BIODEGRADABLE POLYMERS

BACKGROUND OF THE INVENTION

1. Field of Invention

This invention relates to biodegradable polymer composites, multifunctional particles, and methods for making and using them.

2. Description of Related Art

The use of sustainable polymers is a promising solution to reduce the persistence of petroleum-based plastics in the environment. Poly(lactic acid) (PLA) is a renewably-sourced, biodegradable polymer used in additive manufacturing, packaging, and healthcare. However, its degradation is limited outside of municipal composting conditions which comprise temperatures between 40° C. and 60° C. in the presence of at least 40% relative humidity of the soil and the presence of specific microbes able to degrade the material.

While biopolymers have promising degradation profiles compared to petroleum-based polymers, they are limited in their implementation by relatively poor mechanical properties. M. Lackner in his book chapter, *Bioplastics* (Kirk-Othmer Encyclopedia of Chemical Technology. Copyright 2015 John Wiley & Sons, Inc.), shows the substitution potential of selected bioplastics for popular commodity polymers.

TABLE 1

Bioplastics intermaterial substitution opportunities.
Substitution potential: (+++) high, (++) medium,
(+) low, and (−) not foreseen. Reprinted from M. Lackner.

|  | Polyolefins | | | | Other polymers | | | |
|---|---|---|---|---|---|---|---|---|
|  | LDPE | LLDPE | HDPE | PP | PS | PVC | PUR | PET |
| starch polymers | ++ | ++ | ++ | ++ | + | − | ++ | − |
| PLA | + | + | ++ | ++ | ++ | − | − | ++ |
| PHA | ++ | ++ | +++ | +++ | ++ | + | ++ | ++ |
| other polyesters | − | − | − | − | − | − | − | +++ |
| biobased-PE | +++ | ++ | +++ | − | − | − | − | − |

For biopolymers to be considered a viable replacement for fossil-fuel based commodity polymers, the mechanical properties such as modulus, yield strength, elongation and impact toughness need to be brought close to the level of the currently used polymers. For instance, a semi-crystalline grade of PLA has impact strength of 26 J/m which is on par with the brittle polymer polystyrene (PS), and a tensile strength and elastic modulus comparable to polyethylene terephthalate (PET). However, at 6%, the elongation at break of PLA is much lower than the approximately 300% elongation of PET, limiting its competitiveness against PET.

There are many microencapsulated delivery systems disclosed in the art to control the release of the encapsulated active, or provide release when a specific trigger is applied. Such systems have previously suffered from a number of drawbacks.

Matrix particles that provide release of active upon application of shear or friction are generally not environmentally biodegradable. Such capsules are made using reactive monomers that are not Generally Regarded As Safe (GRAS), and are generally unsafe for direct contact with skin or mucous membranes. Such microcapsules are made via chemical processes that generally require long batch cycle times.

Polymers that are used to develop a membrane around the active material need to be crosslinked to provide a sufficient barrier to retain the encapsulated active until its desired release. If such crosslinking results in the formation of non-biodegradable chemical bonds, the lifespan of these polymers in the environment is significantly increased. It is key to achieve crosslinking such that the resultant polymer material or polymer composite can be broken down in the environment.

Biodegradable polymers, such as polysaccharides, are utilized to encapsulate volatile actives. However, these systems prematurely release the encapsulated active, especially in any formulation that contains water.

When polysaccharide-based microcapsules are incorporated into resins, these materials will plasticize the resin as soon as they come in contact with water, or prematurely release the encapsulated payload in the supply chain due to humidity/temperature effects. Moreover, the conventional modified starch systems that are practiced in the encapsulation of flavors and fragrances degrade at temperatures above 160° C. The processing temperature of biodegradable resins in an extrusion or additive manufacturing process is in excess of 200° C. Friable capsules that are disclosed in the art are specifically core/shell capsules. Such core/shell particles contain a pool of oil surrounded by a thin shell. Such core/shell particles are prone to fracture during processing of the biodegradable resin due to the high shear melt processing involved. Hence, there is a need to identify and develop multifunctional additive particle chemistry that protects the liquid degradant, does not prematurely release the degradant during melt processing, can withstand the high temperatures during melt processing, does not plasticize the biodegradable polymer upon exposure to humidity, improves the mechanical properties of the biodegradable polymer, and accelerates the rate of biodegradation of the polymer in a controlled way.

Accordingly, it is desired to provide biodegradable polymer composites having physical properties rivaling or bettering those of polymers that lack biodegradability.

All references cited herein are incorporated herein by reference in their entireties. The citation of any reference is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

BRIEF SUMMARY OF THE INVENTION

A first aspect of the invention comprises a biodegradable resin composite material comprising: a biodegradable polymer resin; and multifunctional particles, wherein: (a) the multifunctional particles comprise 10-70 wt. % of a hydrophobic active ingredient, 21-72 wt. % of a polysaccharide, 3.80-20 wt. % of a crosslinking agent, 1.00-6 wt. % of a catalyst, 0.10-5 wt. % of a silica flow aid, optionally 0.10-5 wt. % of a desiccant, optionally 0.20-20 wt. % of an emulsifier, optionally 1-10 wt. % of a degradation enhancer, and optionally 1-10 wt. % of particle dispersion aids; (b) the multifunctional particles are anhydrous; and (c) the hydrophobic active ingredient is encapsulated in a crosslinked polysaccharide matrix.

A second aspect of the invention comprises a biodegradable resin composite material comprising: a biodegradable polymer resin; and multifunctional particles, wherein the multifunctional particles comprise: (a) at least one epoxy; (b) at least one amine; (c) at least one emulsifier; (d) at least one hydrophobic active; (e) optionally, a tertiary amine catalyst; and (f) optionally, a natural or synthetic clay.

In certain embodiments, the biodegradable polymer resin is a polylactic acid and the biodegradable resin composite material has: (i) an elongation of 6% to 400%; (ii) a Young's modulus of 0.5-6.0 gigapascals; (iii) a Notched Izod Impact strength of 16-650 J/m as measured by ASTM D256 or 2-150 kJ/m$^2$ as measured by ISO 180; and (iv) a yield strength of 25-120 Megapascals.

In certain embodiments, the biodegradable resin composite material has a Rate of Biodegradability that is at least 10% higher than the polylactic acid resin alone.

In certain embodiments, the biodegradable resin composite material further comprises at least one supplemental additive comprising at least one material selected from the group consisting of: impact toughening agents such as natural fibers, inorganic second phase, acrylate-based particles, elastomer particles, thermoset particles, graphene; degradation enhancers such as microbial growth enhancers, fertilizers, lipases, esterases, proteases, amylases, cellulases, materials that contain at least one carboxylic acid moiety, natural fibers, natural particles; nucleating agents such as inorganic particles (clays, talc, sepiolite, calcium carbonate, boron nitrate), aliphatic amides, hydrazine compounds, PDLA, orotic acid, potassium salt of 3,5-bis(methoxycarbonyl)benzenesulfonate (LAK-301), substituted-aryl phosphate salts (TMP-5), N$^{1}$,N$^{6}$-dibenzoyladipohydrazide (TMC-306), N$^1$,N$^{1'}$-(ethane-1,2-diyl)bis(N$^2$-phenyloxalamide) (OXA), nanocrystalline cellulose; plasticizers such as poly(ethylene glycol), poly(ethylene glycol) monolaurate, oligomeric lactic acid, citrate esters (triethyl citrate, acetyltributylcitrate, tributyl citrate, triacetin), glycerol, natural oils, plasticizers plus nanocrystals (chitin or cellulose), oligomeric polyesters and esteramides, oligomeric poly(1, 3-butylene glycol adipate), oligomeric diethyl bishydroxymethyl malonate, poly(1,3-butanediol), dibutyl sebacate, acetyl glycerol monolaurate, poly(propylene glycol); surface tension modifying materials such as anionic surfactants, nonionic surfactants, cationic surfactants, quaternary ammonium salts. hydrophobic active ingredients, nanoclays, silicas, lignin, cellulose, triggered release technology, charcoal, talc, distillers dried grains with solubles, calcium carbonate and polyhydroxyalkanoate.

In certain embodiments, the hydrophobic active ingredient is a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

In certain embodiments, the polysaccharide is a member selected from the group consisting of cellulose; cellulose derivatives such as carboxyalkyl cellulose; natural starches such as potato, tapioca, corn, wheat, sodium alginate, and the like; natural gums such as gum Arabic, gellan gum, xanthan gum, pectin gum, konjac gum; and modified starches such as octenyl succinic acid anhydride modified corn starch.

In certain embodiments, the crosslinking agent is a member selected from the group consisting of dimethyldihydroxy urea, dimethyloldihhyrodyethylene urea, dimethylol urea, dihydroxyethylene urea, dimethylolethylene urea, dimethyldihydroxyethylene urea, citric acid, tartaric acid, malic acid, succinic acid, glutaric acid, citraconic acid, itaconic acid, tartrate monosuccinic acid, maleic acid, poly(acrylic acid), poly(methacrylic acid), poly(maleic acid), poly(methylvinylether-co-maleate) copolymer, copolymers of acrylic acid, copolymers of maleic acid, oxazolines and polyaziridines.

In certain embodiments, the catalyst is a member selected from the group consisting of ammonium chloride, ammonium sulfate, aluminum chloride, magnesium chloride, magnesium nitrate and hypophosphite salts such as sodium hypophosphite, calcium hypophosphite, or magnesium hypophosphite.

In certain embodiments, the silica flow aid is a member selected from the group consisting of fumed silica, precipitated silica, calcium silicate, aluminosilicate, and combinations thereof.

In certain embodiments, the particle dispersion additive comprises a member selected from the group consisting of polycaprolactone, poly(ester amide), polytetramethylene adipatea terephthalate, polybutylene adipate terephthalate, chitosan, collagen, dextran, polyethylene glycol (PEG), polyethylene oxides, sodium alginate, gelatin, poly(L-lysine), poly(aspartic acid), extracellular matrix proteins (Fibronectin, Collagen, Vitronectin, Thrombospondin, Tenascin, Laminin, Entactin), RGD peptides, PLA-PEG block copolymers, and combinations thereof.

In certain embodiments, the amine is dissolved in an aqueous phase or a core phase, and is at least one member selected from the group consisting of linear aliphatic amines, alicyclic amines, aromatic amines, silicone amines, branched amines, polyamines, polyetheramines, polyoxyethylene polyamine, glucosamine, chitosan, chitosan oligosaccharides, diethylenetriamine, ethylenediamine, polyoxypropylene polyamine, fatty amidoamines, fatty amines, and aminated vegetable oil that is a reaction product of unsaturated vegetable oil and cysteamine.

In certain embodiments, the at least one epoxy is at least one member selected from the group consisting of epoxidized vegetable oil, sorbitan glycidyl ether, sorbitol glycidyl ether, polyethylene glycol glycidyl ether, polypropylene glycol glycidyl ether, triglyceride oil with terminal glycidyl ether, trimethylol propane glycidyl ether, pentaerythritol glycidyl ether, and diglycidyl ether of dimer fatty acid.

In certain embodiments, the tertiary amine catalyst (in which active hydrogen attached to nitrogen is completely substituted by either of primary carbon, secondary carbon, tertiary carbon moiety) comprises at least one member selected from the group consisting of aliphatic amines, such as triethanolamine, N,N-dimethylethanolamine, trimethylamine, N,N-dimethylbenzyl amine, 2-(dimethylaminomethyl) phenol, 2,4,6-tris (dimethylaminomethyl) phenol and alicyclic amines such as N-methylpiperidine, N,N-dimethyl piperazine, and 1,4-diazabicyclo[2.2.2]octane.

In certain embodiments, the biodegradable resin composite material includes an emulsifier selected from the group consisting of nonionic emulsifiers, phospholipids, and combinations thereof.

In certain embodiments, the biodegradable resin composite material includes a degradation enhancer selected from the group consisting of microbial growth enhancers, fertilizers, lipases, esterases, proteases, amylases, cellulases, materials that contain at least one carboxylic acid moiety and combinations thereof.

In certain embodiments, the multifunctional particles have a diameter from 0.005 microns to less than 100 microns.

In certain embodiments, the biodegradable resin composite material has 80% biodegradability in the environment.

In certain embodiments, the biodegradable resin composite material is in a form of a packaging product, a textile, an eating utensil, a cup, a plate, a card, a carton, an electrical component, an electrical device, an appliance, a medical product, a hygiene product, a landscaping product, an agricultural product, a solid fabric enhancer, a solid shampoo, a solid antiperspirant, a solid deodorant, a solid detergent, a solid hard surface cleaner, a diaper, a controlled release fertilizer, a controlled release insecticide, a controlled release dye, a film, and articles comprising nanocomposites.

In certain embodiments, the hydrophobic active ingredient comprises a mixture of a hydrophobic active and a material selected from the group consisting of plant waxes, animal waxes, petroleum based waxes, synthetic waxes, mineral waxes, brominated oils, hydrophobically modified inorganic particles, nonionic emulsifiers and oil thickening agents.

In certain embodiments, the biodegradable resin composite material includes a desiccant selected from the group consisting of calcium sulfate, sodium sulfate, calcium silicate, hydrophilic aluminosilicates, magnesium sulfate, silica gel, crosslinked polyacrylates and combinations thereof.

In certain embodiments, the biodegradable resin composite material comprises at least two different types of multifunctional particles, which release different hydrophobic oil compositions and are selected from the group consisting of friction-triggered release microcapsules pH triggered release microcapsules, UV triggered release microcapsules, pH triggered release microcapsules, microbial digestion triggered release microcapsules, enzyme triggered release microcapsules, and water-triggered release microcapsules.

A third aspect of the invention comprises a method for preparing the biodegradable resin composite material of the invention, said method comprising: (a) mixing the hydrophobic active ingredient and degradation enhancer to provide a homogeneous solution; (b) mixing the homogeneous solution with a polysaccharide solution comprising a polysaccharide, a crosslinking agent, a catalyst, an optional emulsifier and water to provide an emulsion; (c) agitating the emulsion to provide a modified emulsion containing hydrophobic active ingredient droplets with a volume average diameter of less than 5 microns; (d) crosslinking the hydrophobic active ingredient droplets in the modified emulsion to form either a core/shell structure or a matrix structure in a further modified emulsion; (e) dewatering the further modified emulsion to provide a powder; (f) adding the silica flow aid to the powder to provide a modified powder; (g) drying the modified powder to provide the multifunctional particles; (h) drying a polylactic acid resin; (i) introducing the polylactic acid resin into a vessel at a temperature effective to provide melted resin; and (j) adding the multifunctional particles to the melted resin under shear to provide the biodegradable resin composite material.

A fourth aspect of the invention comprises a method for preparing the core/shell multifunctional particle of the invention, said method comprising the following steps: (a) preparing the hydrophobic oil phase composition by combining the hydrophobic active core material with oil soluble monomers, oligomers, antioxidants, and emulsifiers; (b) preparing the emulsion by: (i) adding the hydrophobic oil phase into the aqueous phase under high shear agitation or homogenization such that droplets are preferably from about 10 nm to about 75 nm, and more preferably from about 20 nm to about 50 nm in volume average diameter; or (ii) adding water to the hydrophobic oil phase at 900-1200 RPM agitation in a phase inversion process in order to make a pre-emulsion; (c) preparing an aqueous phase comprising either at least one epoxy, or at least one amine, optionally an emulsifier, and optionally a tertiary amine catalyst; and (d) combining the emulsion, at a temperature of 40 to 70° C., and the aqueous phase, at 25° C., and heating the mixture to a temperature of 40 to 70° C. for 2 to 5 hours to achieve an interfacial polymerization reaction.

Not to be limited by theory, the amine added in the aqueous phase can react with several functional groups present in the hydrophobic oil phase, including with epoxy functionality to form amino alcohols.

In certain embodiments, the suspension of controlled release particles is dehydrated in order to create a powder form of the nanoemulsion or nanoparticles. Particle formation aids, such as polysaccharides, are added to enable conversion of the nanosuspension into a powder. In certain embodiments, the polysaccharide is a member selected from the group consisting of octenyl succinic acid anhydride modified starch, gum arabic, xanthan gum, gellan gum, pectin gum, konjac gum, maltodextrins, and carboxyalkyl cellulose.

In certain embodiments, the method further comprises incorporating additives into the melted resin, and the biodegradable resin composite material is a homogeneous mixture of the polylactic acid resin, the multifunctional particles and the additives.

In certain embodiments of the method, the modified powder is heated within a temperature range of 130-185° C. using convective, conductive or radiative heat transfer.

In certain embodiments of the method, the biodegradable resin composite material is melt processed (such as, e.g., by extrusion, thermoforming, or molding) to form a filament, a film, a fiber or other plastic part.

A fifth aspect of the invention comprises a composition comprising the controlled release particles of the invention, wherein the composition is a packaging product, a textile, an eating utensil, a cup, a plate, a card, a carton, an electrical component, an electrical device, an appliance, a medical product, a hygiene product, a landscaping product, an agricultural product, a solid fabric enhancer, a solid shampoo, a solid antiperspirant, a solid deodorant, a solid detergent, a solid hard surface cleaner, a diaper, a controlled release fertilizer, a controlled release insecticide, a controlled release dye, a film, and articles comprising nanocomposites.

In certain embodiments, the composition has at least two controlled release technologies, which release different hydrophobic oil compositions and are selected from the group consisting of neat oils, friction-triggered release microcapsules pH triggered release microcapsules, UV triggered release microcapsules, pH triggered release microcapsules, microbial digestion triggered release microcapsules, enzyme triggered release microcapsules, and water-triggered release microcapsules.

BRIEF DESCRIPTION OF SEVERAL VIEWS OF THE DRAWINGS

The invention will be described in conjunction with the following drawings, wherein:

FIGS. 1A and 1C show precrack morphology of neat 2003D PLA resin with no multifunctional particle. FIGS. 1B and 1D show the same neat 2003D PLA composite with 6 wt % multifunctional particles. Intact multifunctional particles in the cavities can be clearly observed. Such particles provide improved mechanical properties and improved rate of biodegradability.

FIGS. 6A, 6B and 6C show images of a modified ASTM 5338 composting setup. FIG. 6A shows a microbial colony on the surface of compost localized around filaments at Week 3. FIG. 6B shows the microbial colony at Week 6. FIG. 6C shows a filament encased in the microbial colony at Week 8.

FIG. 7 shows a chart comparing the degradability of polylactic acid resin filaments with and without additive as a function of time.

DETAILED DESCRIPTION OF PREFERRED EMBODIMENTS OF THE INVENTION

Glossary

Figure 1:
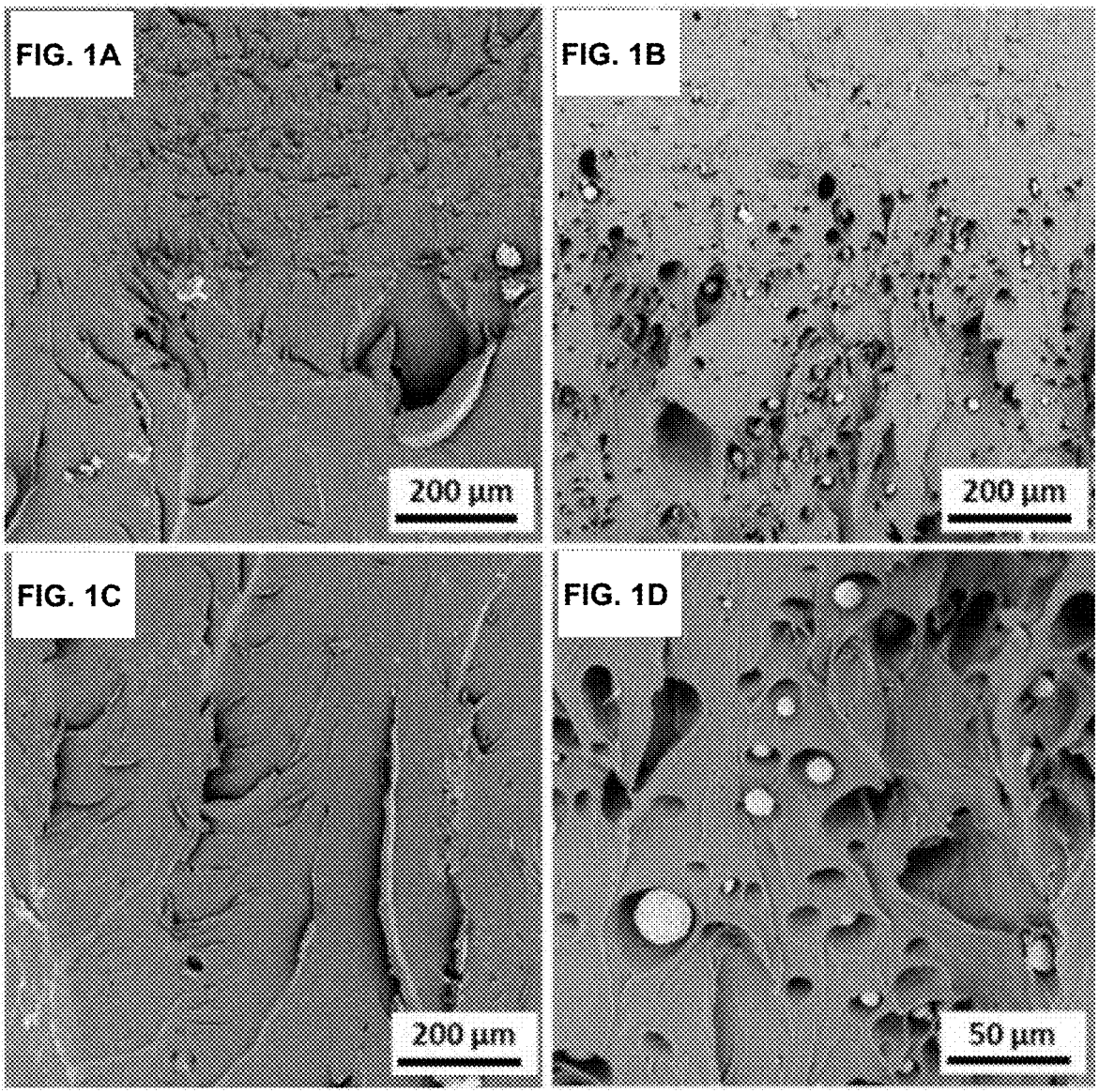
FIGS. 1A, 1B, 1C and 1D show SEM fracture surfaces.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from the group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

The term "substantially free of" refers to 2% or less of a stated ingredient unless specifically stated otherwise. "Free of" refers to no detectable amount of the stated ingredient or thing unless specifically stated otherwise.

As used herein, the terms "a" and "an" mean "at least one".

As used herein, the terms "include", "includes" and "including" are meant to be non-limiting.

Unless otherwise noted, in discussing the commercial applications below, all component or composition levels are in reference to the active portion of that component or composition, and are exclusive of impurities, for example, residual solvents or byproducts, which may be present in commercially available sources of such components or compositions.

Similarly, all percentages and ratios are calculated by weight unless otherwise indicated and are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, unless otherwise noted, "alkyl" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, isopropyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups, the alkyl groups may be the same or different.

The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like.

The dimensions and values disclosed herein are not to be understood as being strictly limited to the exact numerical values recited. Instead, unless otherwise specified, each such dimension is intended to mean both the recited value and functionally equivalent range surrounding that value. For example, a dimension disclosed as "40 mm" is intended to mean "about 40 mm".

As used herein, unless otherwise noted, the terms "capsule", "microcapsule" and "particle" are synonyms, which refer to containers for selectively retaining contents thereof.

As used herein, unless otherwise noted, the terms "shell" and "wall" are synonyms, which refer to barriers at least partially surrounding a core.

Advantages of the Invention

The inventors have developed multifunctional additive particles that will both toughen and accelerate degradation of a biodegradable polymer. Despite progress in the field, the inventors are not aware of any prior multi-functional additives that will both accelerate the degradation of PLA and improve its mechanical properties. Improving the rate of biodegradability has been attempted by many using the same methods as improving toughness; however, very little success has been reported. The present invention addresses both the limited degradation and poor impact toughness by integrating an additive in the biodegradable polymer matrix itself while simultaneously using the particles as impact toughness to improve mechanical properties. A particle additive which improves both toughness and accelerates biodegradation will bring PLA closer to commodity plastics and open more applications for biodegradable polymers, such as in additive manufacturing, specifically fused deposition modeling (FDM).

Encapsulation technology enables the development of multifunctional additives to address multiple issues in a single material. Encapsulation allows for the addition of a degradant directly into the polymer, while simultaneously tuning the mechanical properties through careful design of the particle properties. Encapsulating an active degradant material protects both the degradant and the matrix during melt processing, as well as controlling its release rate, and thus degradation rate. Embedding encapsulated degradants into the polymer also may allow for the polymer degradation rate to be tuned and decoupled from specific environmental conditions. At the same time, proper design of these particles in their size, mechanical properties, and surface chemistry gives the possibility of these additives to also perform as impact modifier particles to increase impact toughness.

The invention comprises a multifunctional additive that makes it feasible to add a liquid degradant species directly into a biodegradable polymer, encapsulated in a controlled-release shell for later delivery into the surrounding matrix. Encapsulating an active degradant material protects both the degradant and the matrix during melt processing, as well as controlling its release rate, and thus degradation rate. Proper design of these particles in their size, mechanical properties, and surface chemistry gives the ability to increase impact toughness. Embedding the encapsulated degradant material into the biodegradable polymer matrix itself improves the impact toughness and accelerates the rate of biodegradation of printed parts produced by additive manufacturing. Furthermore, the multifunctional additive itself is preferably environmentally biodegradable, has low hygroscopicity, is water insoluble, and/or can be made via an economical process.

Multifunctional Particles

The invention addresses one or more of the prior art deficiencies described above by providing multifunctional particles having controlled release characteristics. The particles are particularly well-suited for use in encapsulation of hydrophobic, nonpolar materials.

In certain embodiments, the multifunctional particle comprises 10-70 wt. % of a hydrophobic active ingredient, 21-72 wt. % of a polysaccharide, 3.80-20 wt. % of a crosslinking agent, 1.00-6 wt. % of a catalyst, 0.10-5 wt. % of a silica flow aid, optionally 0.10-5 wt. % of a desiccant, optionally 0.20-20% emulsifier, and optionally 1%-10% of a degradation enhancer, wherein the multifunctional particles are anhydrous and the hydrophobic active ingredient is encapsulated in a crosslinked polysaccharide matrix.

The hydrophobic active ingredient is a hydrophobic substance that is active (or effective) to provide a desired effect, alone or in combination with other substances and/or conditions. It is present in the particles in an amount effective to provide a desired effect. The amount can be, e.g., from 1 wt. % or 5 wt. % or 10 wt. % to 25 wt. % or 50 wt. % or 70 wt. % or 80 wt. %.

The hydrophobic active ingredient is preferably a member selected from the group consisting of a flavorant, a fragrance, a chromogen, a dye, an essential oil, a sweetener, an oil, a pigment, an active pharmaceutical ingredient, a moldicide, a herbicide, a fertilizer, a phase change material, an adhesive, a vitamin oil, a vegetable oil, a triglyceride and a hydrocarbon.

Suitable flavorants include but are not limited to oils derived from plants and fruits such as citrus oils, fruit essences, peppermint oil, clove oil, oil of wintergreen, anise, lemon oil, apple essence, and the like. Artificial flavoring components are also contemplated. Those skilled in the art will recognize that natural and artificial flavoring agents may be combined in any sensorially acceptable blend. All such flavors and flavor blends are contemplated by this invention. Carriers may also be mixed with flavors to reduce the intensity, or better solubilize the materials. Carriers such as vegetable oils, hydrogenated oils, triethyl citrate, and the like are also contemplated by the invention.

Suitable fragrances include but are not limited to compositions comprising materials having an Log P (logarithm of octanol-water partition coefficient) of from about 2 to about 12, from about 2.5 to about 8, or even from about 2.5 to about 6 and a boiling point of less than about 280° C., from about 50° C. to about less than about 280° C., from about 50° C. to about less than about 265° C., or even from about 80° C. to about less than about 250° C.; and optionally, an ODT (odor detection threshold) of less than about 100 ppb, from about 0.00001 ppb to about less than about 100 ppb, from about 0.00001 ppb to about less than about 50 ppb or even from about 0.00001 ppb to about less than about 20 ppb. Diluents that are miscible in the fragrance oil, and act to reduce the volatility of the fragrance oil, such as isopropyl myristate, iso E super, triethyl citrate, vegetable oils, hydrogenated oils, and the like are also contemplated by the invention.

Suitable chromogens include but are not limited to Michler's hydrol, i.e. bis(p-dimethylaminophenyl)methanol, its ethers, for example the methyl ether of Michler's hydrol and the benzylether of Michler's hydrol, aromatic sulfonic and sulfinic esters of Michler's hydrol, for example the p-toluenesulfinate of Michler's hydrol, and derivatives of bis(p-dimethylaminophenyl)methylamine, for example N[bis(p-dimethylaminophenyl)methyl]morpholine.

Suitable dyes include but are not limited to Sudan Red 380, Sudan Blue 670, Baso Red 546, Baso Blue 688, Sudan Yellow 150, Baso Blue 645, Flexo Yellow 110, and Flexo Blue 630, all commercially available from BASF; Oil Red 235, commercially available from Passaic Color and Chemical; Morfast Yellow 101, commercially available from Morton; Nitro Fast Yellow B, commercially available from Sandoz; Macrolex Yellow 6G, commercially available from Mobay. Preferred dyes are those having good solubility in aromatic solvents.

Suitable essential oils include but are not limited to those obtained from thyme, lemongrass, citrus, anise, clove, aniseed, roses, lavender, citronella, eucalyptus, peppermint, camphor, sandalwood, cinnamon leaf and cedar. Essential oils that exhibit antimicrobial properties are also contemplated by this invention.

Suitable sweeteners include but are not limited to materials that contain varying amounts of disaccharide and/or fructose; erythritol, honey, and/or evaporated cane juice; and rebaudioside A, and the like Suitable pigments include but are not limited to pearl pigments of mica group such as titanium dioxide-coated mica and colored titanium dioxide-coated mica; and pearl pigments of bismuth oxychlorides such as colored bismuth oxychloride. Such pigments are available on the market under various trade names: Flamenco series (by the Mearl Corporation), TIMIRON COLORS (by MERCK) as titanium dioxide-coated mica, Timica Luster Pigments (by MEARL). Cloisonee series (by MEARL), COLORON series (by MERCK), SPECTRA-PEARL PIGMENTS (by Mallinckrodt) as colored titanium dioxide-coated mica and MIBIRON COLORS series (by MERCK) as colored bismuth oxychloride.

Suitable active pharmaceutical ingredients include but are not limited to water insoluble materials that have a melting point below 50° C.

Suitable moldicides include but are not limited to an inorganic biocide selected from the group consisting of a metal, a metal compound and combinations thereof. Preferably, the inorganic biocide is copper, cobalt, boron, cadmium, nickel, tin, silver, zinc, lead bismuth, chromium and arsenic and compounds thereof. More preferably, the copper compound is selected from the group consisting of copper hydroxide, cupric oxide, cuprous oxide, copper carbonate, basic copper carbonate, copper oxychloride, copper 8-hydroxyquinolate, copper dimethyldithiocarbamate, copper omadine and copper borate. Fungicidal compounds which in the present invention include isothiazolone compounds. Typical examples of isothiazolone compounds include but not limited to: methylisothiazolinone; 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 2-ethyl-4-isothiazoline-3-one, 4,5-dichloro-2-cyclohexyl-4-isothiazoline-3-one, 5-chloro-2-ethyl-4-isothiazoline-3-one, 2-octyl-3-isothiazolone, 5-chloro-2-t-octyl-4-isothiazoline-3-one, 1,2-benzisothiazoline-3-one, preferably 5-chloro-2-methyl-4-isothiazoline-3-one, 2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, etc., more preferably 5-chloro-2-methyl-4-isothiazoline-3-one, 2-n-octyl-4-isothiazoline-3-one, 4,5-dichloro-2-n-octyl-4-isothiazoline-3-one, 1,2-benzisothiazoline-3-one, chloromethylisothiazolinone, 4,5-Dichloro-2-n-octyl-3 (2H)-isothiazolone and 1,2-benzisothiazolin-3-one.

Suitable herbicides include but are not limited to 2-(2-chloro-4-methylsulfonylbenzoyl)-1,3-cyclohexanedione, 2-(2-nitrobenzoyl)-4,4-dimethyl-1,3-cyclohexanedione, 2-(2-(nitrobenzoyl)-5,5-dimethyl-1,3-cyclohexanedione, and their 2-benzoylcyclohexanedione derivatives, in addition to those listed in WO2006024411A2.

Suitable phase change materials include but are not limited to a crystalline alkyl hydrocarbon which is comprised of one or more crystalline straight chain alkyl hydrocarbons having 14 or more carbon atoms and heats of fusion greater than 30 cal/g. The melting and freezing point of the alkyl hydrocarbon is in the range of 0° to 80° C., preferably 5° to 50° C., and most preferably, 18° to 33° C. Representative materials are crystalline polyolefins such as polyethylene, polypropylene, polybutene, crystalline polystyrene, crystalline chlorinated polyethylene and poly(4-methylpentene-1). Crystalline ethylene copolymers such as ethylene vinylacetate, crystalline ethylene acrylate copolymers, ionomers, crystalline ethylene-butene-1 copolymers and crystalline ethylene-propylene copolymers are also useful polyolefins. Preferably, the polyolefins are crosslinked such that they are form stable upon heating above their crystalline melting point. Suitable adhesives include but are not limited to compositions comprising an elastomer and a tackifying agent. The elastomer adds toughness to the adhesive film and also is responsible for at least part of the required initial pressure-sensitive tackiness. The elastomeric materials are water insoluble and are inherently tacky or are capable of being rendered tacky by mixture with compatible tackifying resins. Preferably the elastomers are natural rubber or butadiene or isoprene synthetic polymers or copolymers such as butadiene-isobutylene copolymers, butadiene-acrylonitrile copolymers, butadiene-styrene copolymers, polychloroprene or similar elastomers. A combination of the above elastomers may be utilized. Preferred tackifying resin materials include unsaturated natural resins such as rosin or derivatives thereof, such as rosin esters of polyols such as glycerol or pentaerythritol, hydrogenerated rosins or dehydrogenerated rosins Suitable vitamin oils include but are not limited to fat-soluble vitamin-active materials, pro vitamins and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such materials. The oil-soluble vitamin oil concentrate may be a high potency fish liver oil containing vitamin A and/or D, a synthetic vitamin A palmitate and/or acetate concentrated in an oil solution, vitamin D, or D either concentrated in oil solution or as an oleaginous resin, vitamin E (d-alpha tocopheryl acetate) in an oil solution, or vitamin K in oil solution, or beta-carotene as a crystalline oil suspension in oil. Suitable vegetable oils include but are not limited to oils derived from palm, corn, canola, sunflower, safflower, rapeseed, castor, olivek, soybean, coconut and the like in both the unsaturated forms and hydrogenated forms, and mixtures thereof.

Suitable triglycerides include but are not limited to those disclosed in U.S. Pat. No. 6,248,909B1.

Suitable hydrocarbons that can be the active or can be used in combination with the active in order to change the physical or chemical properties of the active, include but are not limited to, waxes, density modifiers, surface tension modifiers, melting point modifiers, viscosity modifiers, and mixtures thereof. Examples include animal waxes such as beeswax, plant waxes such as carnauba wax, candelilla wax, bayberry wax, castor wax, tallow tree wax, soya wax, rice bran wax, hydrogenated rice bran wax, soya wax, hydrogenated soya wax, hydrogenated vegetable oil. Examples of petroleum derived waxes are paraffin waxes and microcrystalline waxes. An example of synthetic wax is polyethylene wax. Examples of materials that can modify the density of the active phase in the particle are brominated vegetable oil, nanoclays such as montmorrilonite or kaolin, hydrophobically modified clays, hydrophobically modified precipitated silicas or fumed silicas. Examples of materials that can alter the surface tension of the active phase in the particle are nonionic emulsifiers such as polysorbate-type nonionic surfactant (e.g. Tween™), alcohol ethoyxlate based surfactants (e.g. Genapol™). Examples of oil thickening agents are waxes mentioned above, modified organopolysiloxanes, silicone gums, hydrogenated castor oil, paraffin oils, polyolefins, and the like.

The polysaccharide is present in the particles in an amount effective to provide a coating and/or matrix having the desired structural properties. The amount can be, e.g., from 5 wt. % or 10 wt. % or 21 wt. % or 25 wt. % to 50 wt. % or 64 wt. % or 72 wt. % or 80 wt. %.

Polysaccharides having emulsifying and emulsion stabilizing capacity are preferred. The polysaccharide is preferably a member selected from the group consisting of octenyl succinic acid anhydride modified starch, gum arabic, xanthan gum, gellan gum, pectin gum, konjac gum and carboxyalkyl cellulose. Octenyl succinic acid anhydride modified starches are useful polysaccharides when the melt processing temperatures are lower than 160 degrees Centigrade. Carboxyalkyl celluloses are preferred when the melt processing temperature exceeds 160 degrees Centigrade.

The crosslinking agent is present in the matrix and hybrid particles of the invention in an amount effective (in the presence of the catalyst) to crosslink the polysaccharide to an extent effective to provide the particles with desired durability. The amount can be, e.g., from 1 wt. % or 2 wt. % or 3.80 wt. % or 5 wt. % to 8 wt. % or 10 wt. % or 12 wt. % or 15 wt. %.

The crosslinking agent is preferably a member selected from the group consisting of dimethyldihydroxy urea, dimethyloldihhyrodyethylene urea, dimethylol urea, dihydroxyethylene urea, dimethylolethylene urea, dimethyldihydroxyethylene urea, citric acid, tartaric acid, malic acid, succinic acid, glutaric acid, citraconic acid, itaconic acid, tartrate monosuccinic acid, maleic acid, poly(acrylic acid), poly(methacrylic acid), poly(maleic acid), glyceryl stearate citrate, poly(methylvinylether-co-maleate) copolymer, copolymers of acrylic acid and copolymers of maleic acid.

The catalyst is present in the matrix and hybrid particles of the invention in an amount effective to catalyze the crosslinking of the polysaccharide to an extent effective to provide the particles with desired durability. The amount can be, e.g., from 0.1 wt. % or 0.5 wt. % or 1 wt. % or 2 wt. % to 2.5 wt. % or 5 wt. % or 6 wt. % or 7 wt. %.

The catalyst is preferably a reducing agent and/or electron donor, and is more preferably a member selected from the group consisting of ammonium chloride, ammonium sulfate, aluminum chloride, magnesium chloride, magnesium nitrate and sodium hypophosphite.

The silica flow aid is present in the particles in an amount effective to minimize or eliminate clumping and the presence of flakes in the particles. The amount can be, e.g., from 0.05 wt. % or 0.10 wt. % or 0.5 wt. % or 1 wt. % to 2.5 wt. % or 5 wt. % or 7.5 wt. % or 10 wt. %.

The silica flow aid is preferably a precipitated silica, a dried colloidal silica, and more preferably a fumed silica. Hydrophobic silicas are preferred. Silicas that have a surface area greater than 60 m$^2$/g are more preferred. Preferred fumed silicas include AEROSIL R 812. Preferred precipitated silicas include SYLOID 244 and SIPERNAT D17, which is hydrophobic and ZEOTHIX, which is hydrophilic. Alternatively, the silica flow aid comprises calcium silicate, such as Hubersorb 250 or 600 grades sold by Huber Corporation. Alternatively, the silica flow aid is an aluminosilicate such as the Zeolex grades sold by Huber Corporation. Alternatively, the silica flow ad is a dried colloidal silica such as the Ludox grades sold by W.R. Grace.

Optionally a desiccant is added to the powder to absorb the moisture that is released from the particle during heating, such that the moisture does not act to plasticize the particle and form large aggregates. Suitable desiccants include but are not limited to calcium sulfate, sodium sulfate, calcium silicate, hydrophilic aluminosilicates, magnesium sulfate, silica gel, crosslinked polyacrylates, and the like. It is desirable to have the desiccant particle size at least 5 times the median particle size of the powder being heated, such that after the powder heating process, the desiccants can be removed via sieving. The amount can be, e.g., from 0.05 wt. % or 0.10 wt. % or 0.5 wt. % or 1 wt. % to 2.5 wt. % or 5 wt. % or 7.5 wt. % or 10 wt. %.

The emulsifier is present in the multifunctional particles in an amount from 0.2 wt. % or 1.5 wt. % or 1.5 wt. % or 5 wt. % to 5 wt. % or 10 wt. % or 10 wt. % or 20 wt. %.

In certain embodiments, the emulsifier is a member selected from the group consisting of nonionic emulsifiers selected from polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, sorbitan esters, monoglycerides; phospholipids preferably selected from lecithins, preferably fluid, deoiled, or fractionated lecithins. Preferred lecithins have greater than 20% by weight of phosphatidylcholine; and combinations thereof.

The degradation enhancer is present in the multifunctional particles in an amount from 0.5 wt. % or 1 wt. % or 1.5 wt. % or 5 wt. % to 5 wt. % or 7.5 wt. % or 10 wt. %.

In certain embodiments, the degradation enhancer is a member selected from the group consisting of microbial growth enhancers; fertilizers; lipases, esterases, proteases, amylases, cellulases; materials that contain at least one carboxylic acid moiety, and combinations thereof.

In certain embodiments, the amine (as —NH$_2$ and or —NH prior to reaction but as tertiary amine after reaction) is present in particles of the invention in an amount effective to react with the epoxy moieties to an extent effective to provide the particles with desired durability. The amount of amine on a dry basis (weight of nitrogen in the form of tertiary amine per weight of dry matter in the suspension) can be, e.g., from 0.20 wt % or 0.25 wt % or 0.30 wt % or 0.35 wt. %.

In certain embodiments, the epoxy is at least one member selected from the group consisting of epoxidized vegetable oil, sorbitan glycidyl ether, sorbitol glycidyl ether, polyethylene glycol glycidyl ether, polypropylene glycol glycidyl ether, triglyceride oil with terminal glycidyl ether, trimethylol propane glycidyl ether, pentaerythritol glycidyl ether, and diglycidyl ether of dimer fatty acid.

In certain embodiments, the epoxy (as secondary OH after reaction) is present in particles of the invention in an amount effective to react with amine moiety. The amount of epoxide a dry basis (weight of secondary OH only resulting from reaction per weight of dry matter in the suspension) can be, e.g., from 0.50 wt. % or 0.65 wt. % or 0.70 wt. % or 0.85 wt. %.

The multifunctional particles are preferably spherical but non-spherical shapes are also within the scope of the invention. The particles preferably have a diameter from 0.005-250 microns, or from 0.1 microns to less than 100 microns.

In certain embodiments, the biodegradable resin composite material has a biodegradability greater than 25% or greater than 75% or greater than 80%.

The biodegradable resin composite material preferably has a Rate of Biodegradability that is at least 10% to about 15%, from about 15% to about 25%, from about 25% to about 50%, or from about 50% to about 70% higher than a polylactic acid resin which is an ingredient of the composite.

Method of Making the Particles

The multifunctional particles of the invention are provided by a method comprising: mixing the hydrophobic active ingredient and degradation enhancer to provide a homogeneous solution; mixing the homogeneous solution with a polysaccharide solution, comprising a polysaccharide, a crosslinking agent, a catalyst, an optional emulsifier and water to provide an emulsion; agitating the emulsion to provide a modified emulsion containing hydrophobic active ingredient droplets with a volume average diameter of less than 5 microns; applying conditions to achieve crosslinking of the emulsion droplets to form either a core/shell type of structure or matrix type of structure; optionally, mixing with the emulsion a colloidal suspension of nanoparticles that may act as a drying or processing aid; dewatering the emulsion to provide a powder; adding silica flow aid to the powder to provide a modified powder; and optionally heating the modified powder to form the multifunctional particles.

The emulsion is agitated to provide oil droplets in the emulsion which are preferably 0.0035 to 10 microns, and more preferably 0.05 to 5 microns in volume average diameter.

A potential process to dewater the suspension of particles is spray drying. Spray drying of the emulsion is preferably conducted in a co-current spray dryer, at an inlet air temperature of 325 to 415° F. (163-213° C.), preferably from 355 to 385° F. (179-196° C.) and an outlet air temperature of 160 to 215° F. (71-101° C.), preferably from 175-195° F. (79-91° C.).

An alternative process to dewater the suspension of particles is via the use of convection oven, vacuum ovens, or drum drying using a kiln. The operating temperature for drying under these conditions can be from 120 to 185° C., more preferably from 120 to 150° C.

The silica flow aid is added to the dry powder to improve the flowability of the powder. Addition of the silica flow aid minimizes the agglomeration of particles during the curing process, in cases where the crosslinking of the particles is achieve post-dewatering, and surprisingly reduces the volatility of the encapsulated active. The exact mechanism of interactions is not understood; however, thermal analysis clearly shows a desired reduction in volatility of the encapsulated active.

Without the addition of silica, the powder would agglomerate during the curing process. To achieve a particle size less than 100 microns, it would be necessary to grind the agglomerated powder, which would be detrimental to the particles, because it could lead to fracture of the particles and premature release of the encapsulated active material.

The powder is then optionally heated to achieve the desired interaction between polysaccharide, crosslinking agent and the catalyst and provide a multifunctional particle that can provide friction-triggered release, water triggered release, enzyme triggered release, or microbial-digestion triggered release of the encapsulated active.

The modified powder is preferably heated with a temperature range of 120-185° C. for a preferred curing time within the range of 3-60 minutes, more preferably 5-30 minutes. Insufficient curing may occur at temperatures below 130° C. and/or for lesser curing times. In order to minimize the degradation of the matrix components, minimize premature fracture of the particle, and minimize volatile loss of encapsulated active materials, the maximum curing temperature should not exceed 185° C. Curing conditions can be adjusted to achieve a desired reduction in particle solubility in water, and desired release profile of the encapsulated active.

Curing of the particles can be achieved by any suitable heating means. There are three primary methods of heat transfer: convective, conductive, and radiative. Convective heat transfer uses air to fluidize the particles, and the temperature of the air is manipulated to achieve the desired heating. Conductive heat transfer utilizes either electric heating in a kiln, or oil heating in a jacketed paddle mixer (auger mixer, cement mixer, ribbon blender, U-trough mixer, and the like). The powder is rotated in the mixer and heating occurs by transfer of heat from the metal surface of the mixer to the powder touching that surface. Radiative heat transfer utilizes infrared waves, radio frequency waves, microwaves to achieve the desired heating. Any of these methods can be used to achieve the desired heat treatment of the particle. Suitable heating means include but are not limited to one or more of the following: oven, rotary infrared dryers, microwave radiative dryers, radio frequency radiative dryers, kiln or calciner, steam tube dryers, tray dryers, fluid bed dryers, granulators, baking ovens, serpentine ovens, jacketed auger mixers, jacketed ribbon blenders, and the like.

Gentle agitation is preferably provided during curing to minimize fracture of the particles.

Biodegradable Polymer Resin

Biodegradable polymers are those in which significant loss to their physical and mechanical properties are caused by chemical changes brought about by specific environmental conditions such as heat, light, oxygen, or microorganisms. Biodegradable polymers are susceptible to degradation by enzymes produced by microorganisms such as fungi, bacteria, or algae. All such biodegradable polymers are contemplated by the invention. Polylactic acid degrades completely to nontoxic components, with $CO_2$, water, and humus being the end products.

Biodegradation of polymers is generally a two-step process, in which the initial breakdown of the polymer is carried out by hydrolysis which lowers the bulk molecular weight by chain scission. Hydrolysis continues until the oligomers produced are small enough to be consumed by microorganisms, producing $CO_2$, water, and metabolic products.

The initial abiotic hydrolysis is considered by many studies to be the main and rate-limiting biodegradation step, as high humidity and temperature enables the cleavage of the ester linkages by water uptake causing reduction in molecular weight.

The second step of degradation involves assimilation and use of the acid oligomer fragments by microorganisms, releasing carbon dioxide, water, and metabolic products.

In certain embodiments of the invention, the biodegradable polymer resin comprises one or more of carboxy methylcellulose, polyhydroxybutyrate, polybutylenesuccinate, polycaprolactone, thermal polyaspartate, polylactic acid, and the like. The preferred biodegradable polymer resin is polylactic acid.

In certain embodiments, the biodegradable resin composite comprises a polylactic acid composite material having an elongation of 6% to 85%, a Young's modulus 0.5-4.0 Gigapascals, and a Yield Strength 30-60 Megapascals.

Compositions Containing the Particles

The invention further comprises compositions comprising the multifunctional particles. Such compositions include but are not limited to a packaging product, a textile product, food service ware such as utensils, cups, plates, and the like, cards, cartons, electronics and appliances, medical product, hygiene products, landscape products, agricultural products, a solid fabric enhancer, a solid shampoo, solid antiperspirant, solid deodorant, solid detergent, solid hard surface cleaner, a diaper, a controlled release fertilizer, a controlled release insecticide, a controlled release dye, films, articles comprising nanocomposites.

EXAMPLES

The invention will be illustrated in more detail with reference to the following Examples, but it should be understood that the present invention is not deemed to be limited thereto.

Materials and Methods

In order to test a biodegradable polymer composite, 3D printer filament is extruded to observe the multifunctional particle survival during extrusion and dispersion in the polymer matrix. Dried multifunctional particles were prepared for melt compounding by sieving through a 44 micron wire mesh sieve and dried at 80° C. overnight. NatureWorks Ingeo Biopolymer 2003D grade poly(lactic acid) was used as the matrix polymer. The molecular weight of this grade is 200-250 kDa. Particles were mixed into the dried pellets or powders (as indicated) before melt compounding at the weight percent indicated by the particle formula.

Figure 2:
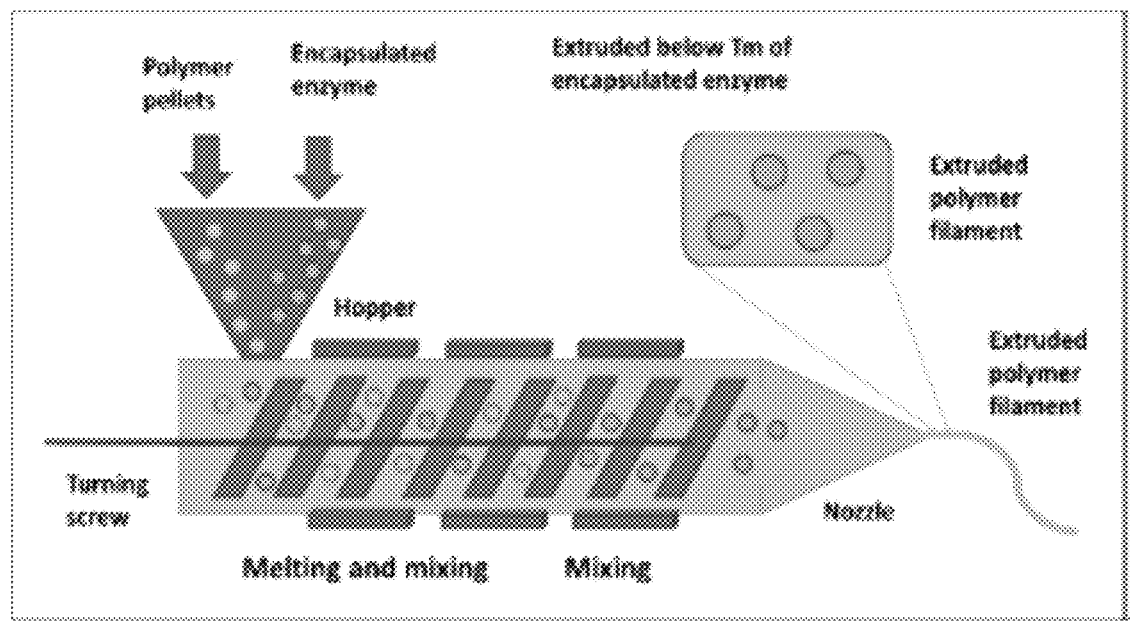
FIG. 2 shows an embodiment of a extrusion setup used to make biodegradable polymer composites.

The process shown in FIG. 2 was utilized to extrude the test filaments. In summary, a ¾ inch single-screw Brabender Processing Plasti-Corder PL 2000 extruder fitted with a single-stage mixing screw of L/D 20:1 was used to extrude filament to a diameter of approximately 1.75 mm. Unless otherwise specified, a nominal feed zone temperature of 150° C., barrel temperature of 160° C., and die temperature of 160° C., and a screw speed of 28 rpm were used. The filament was water cooled with the water bath held at room temperature. Filaments are named by the matrix grade of either 4043D or 2003D, followed by the particles with which they are filled, and the weight percent of particle additives.

The extruded filaments containing additive particles were screened for particle suitability by observing particle dispersion in the matrix and off-gassing of particles during extrusion. Particle formulas that were well-dispersed and did not appear to degrade during extrusion were subjected to tensile testing in filaments, and for biodegradation properties. Particle formulas meeting acceptability criteria for tensile toughness were used for further testing in fracture mechanics of 3D printed specimens.

Figure 3A:
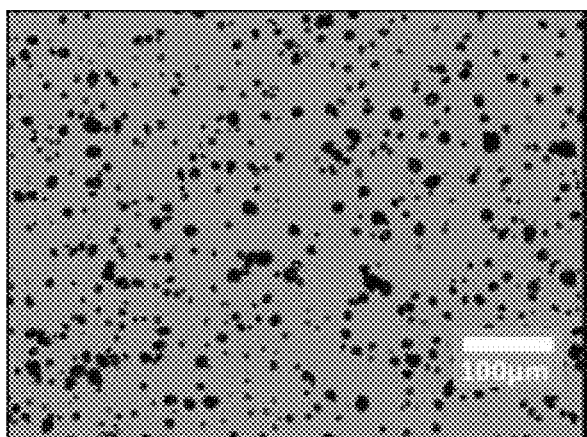
FIGS. 3A and 3B show optical micrographs comparing good particle dispersion (FIG. 3A) with particle agglomeration (FIG. 3B) in PLA.
Figure 3B:
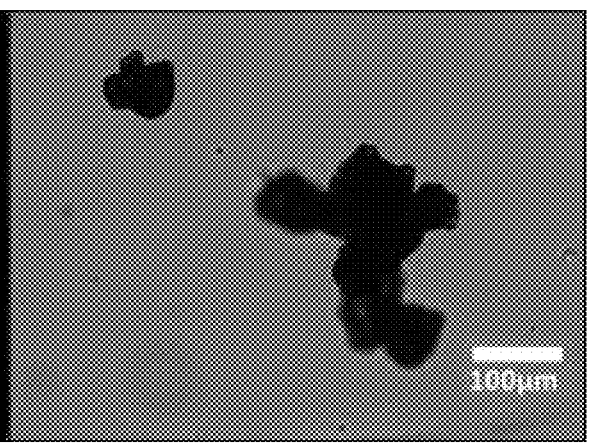

Particle dispersion in the matrix and survival through extrusion were observed for each test particle and used to screen shell materials. A successful composite filament, and thus a successful particle, capable of being used for further testing has tight tolerances of filament diameter, complete dispersion of particles in the matrix, and no obvious degradation of capsules in the filament. The dispersion of the particles in the PLA matrix was determined by visual inspection and by petrography. The specimens were inspected for bonding between the matrix and the particle and for particle integrity. FIGS. 3A and 3B show two polysaccharide-based particles, one with favorable dispersion properties and one in which the particles remain aggregated within the matrix. Particle 1A of Example 1 below dispersed evenly in the PLA, thought to be due to a compatibilizing coating added during spray drying as well as the surface chemistry of the particle itself. FIG. 3A shows an optical micrograph showing good particle dispersion, while FIG. 3B shows an optical micrograph showing particle agglomeration in PLA.

Tensile testing was used to screen the experimental particles by their effect on filament properties. The quantities monitored were yield strength, Young's modulus, and elongation at break. See Table 2 below. Although sample parameters can affect the results, an increase in these quantities, particularly the elongation at break, is considered favorable as it indicates an overall improvement in mechanical properties. Elongation at break greater than neat PLA filament was considered a passing result. While tensile toughness does not predict impact toughness, it gives information about the integrity of the filament when filled with a specific particle type. These filaments are tested at a strain rate of 0.05 mm/mm·min, rather than 0.1 mm/mm·min of most other tensile experiments contained in this work.

TABLE 2

| Average tensile properties of filaments with 6 wt % particles (0.05 mm/mm · min) Parameter | Modulus (GPa) | Yield Strength (MPa) | Elongation at Break |
|---|---|---|---|
| Filament 2-0-0 (no multifunctional particle) | 2.8 | 34.1 | 4.4% |
| Filament 2-1A-6 (6 wt % multifunctional particle) | 4.1 | 26.9 | 29% |

Other filaments show significant increase in elongation at break, when compared to a polylactic acid resin that does not comprise any multifunctional particle. See Table 3 below. Although there is some decrease in Young's Modulus and Yield Strength, the significant increase in elongation at break improves the ability to form the polylactic acid composite material into consumer usable products.

TABLE 3

| Parameter | Filament 4-0-0 | Filament 4-1A-6 | Filament 4-1A/S-6 |
|---|---|---|---|
| Young's Modulus (GPa) | 1.60 ± 0.12 | 1.35 ± 0.20 | 1.41 ± 0.13 |
| Yield Strength (MPa) | 58.2 ± 4.8 | 35.8 ± 1.6 | 34.9 ± 2.9 |
| Elongation at Break (%) | 9.34 ± 17 | 47.8 ± 22 | 78.2 ± 41 |

Thermogravimetric Analysis

A Thermogravimetric Analysis platinum pan is exposed to a Bunsen burner to remove any residue from the pan. Approximately 5 milligrams of sample is weighed onto a pan of a Thermal Gravimetric Analyzer (Model TGA Q500). Next the sample is exposed to a temperature ramp that comprises an initial temperature of 25° C., and a heating ramp of 10° C. per minute, to a final temperature of 600° C.

Differential Scanning calorimetry

Approximately 5 milligrams of sample is weighed onto a pan of a Differential Scanning calorimeter (Model DSC Q2000) and hermetically sealed. The sample pan is then exposed to a temperature scan that comprises in the first cycle heating from 25° C. to 200° C. at a ramp rate of 10° C./min, cooled to 0° C. at a rate of 10° C./min and the second cycle immediately performed from 0° C. to 200° C. with a ramp rate of 10° C./min and cooled to 25° C. at a rate of 10° C./min. A graph of heat flow versus temperature provides insights into thermal transitions that occur in the material.

TA Universal Analysis software is used to analyze the scans. The cold crystallization peak is included in the calculation of percent crystallinity for the first heating cycle to determine the initial crystallinity of the filament sample after processing or testing. For the second heating curve, only the melting peak was used to calculate percent crystallinity, and the crystallization peak ignored. This was done to determine the maximum percent crystallinity of the material at the cooling rate and heating rate of 10° C./min. An enthalpy of fusion of 93.1 J/g for 100% crystalline PLA was used to calculate the percent crystallinity.

Scanning Electron Microscopy

A Phenom Pure (Nanoscience Instruments Model PW-100-019) Scanning Electron Microscope is used to understand the particle morphology, and nature of particle deposits on fabrics. PELCO tabs carbon tape (12 mm OD, Ted Pella product number 16084-1) is applied to an aluminum specimen mount (Ted Pella Product No 16111). Next, the powder sample is placed onto the carbon tape using a transfer spatula or forceps. Excess powder is removed by blowing Dust-Off compressed gas onto the sample. The stub is then left in a desiccator under vacuum for 16 hours to flash off any volatiles. The sample is then placed into the Phenom Pure, and imaged to visualize particle or material surface morphology.

Mechanical Testing

Tensile testing is used to observe the effect of the experimental particles on the properties of the composite material formed from the matrix polymer and additive particles. The testing is performed directly on extruded composite filament and stress-strain curves generated to obtain yield strength, Young's modulus, and elongation at break. Tensile testing is performed using a modified ASTM D638-14 (Standard Test Methods for Tensile Properties of Plastics) on a screw-driven Instron 5567 outfitted with rope grips (Bollard Style, Mark-10 Corporation) at an initial strain rate of 0.1 mm/min·min. Instron Bluehill 3 software is used to collect and export data. Impact toughness is measured as Notched Izod Impact strength using methods ASTM D256 or ISO 180.

Biodegradability

Biodegradability testing is carried out according to protocol OECD 301D. 5 mg/L material is placed into BOD bottles in water collected from the Lehigh River (Bethlehem, Pa.). The bottles are measured for dissolved oxygen at 0 days and 28 days.

Compostability

PLA filaments extruded with additives were subjected to degradation testing as an additional screening for relative composting rates. Compostability testing was performed using a modified ASTM D5338-15 (Standard Test Method for Determining Aerobic Biodegradation of Plastic Materials Under Controlled Composting Conditions, Conditions, Incorporating Thermophilic Temperatures) soil contact procedure. Mature compost was obtained from a municipal composter (First Regional Compost Authority, Northampton, Pa.) and incubated in aerobic conditions, with loose lids, at 58° C. while maintaining approximately 50% moisture content of the compost. Samples were weighed and placed into soil at approximately 6:1 soil to sample by weight, and three were removed from each jar each week without replacement. The test setup is shown in FIG. 6A. Samples were desiccated at least 4 days before testing.

Dilute Solution Viscometry

A stock solution of 1 g/dL of PLA in THF was prepared by heating to 55° C. in a closed vessel. Solutions were filtered through a PVDF filter with 0.45 micron pore size before measurement. Degradation samples for testing were prepared in the concentration of 0.2 g/dL. Size 25 Cannon Ubbelohde Viscometers were suspended in a water bath held constant at 30° C. The time for the liquid level to travel between the two level lines of the capillary viscometer was recorded and converted to relative viscosity. Relative viscosity, or viscosity ratio is calculated using $\eta_{rel} = t t_0 = \eta \eta_s$ where t is the time for the dilute sample to travel through a capillary viscometer, $t_0$ is the time for the solvent, $\eta$ is the sample viscosity and $\eta_s$ is the solvent viscosity.

X-Ray Diffraction

X-Ray Diffraction (XRD) was used to characterize the crystallinity of the samples before and after exposure to composting conditions. Samples were ground into a powder using a mortar and pestle and measured in a Rigaku Mini-FlexII Desktop X-ray Diffractometer. Continuous sampling, with an angle of 10-50 degrees and a sampling width of 0.010 units, a scan speed of 1.0, voltage of 30 kV, and current of 15 mA. Spectra were collected and analyzed using the Rigaku Standard Measurement software and Excel.

FTIR

Functional group signal changes are detected using Fourier Transform Infrared Spectroscopy (FTIR). FTIR analyses were performed on a PerkinElmer Spectrum 100 FT-IR Spectrometer equipped with an ATR sampling fixture. Surfaces were analyzed in the attenuated total reflection mode (ATR). Spectrum analyses were performed on PerkinElmer Spectrum software in the 4,000-650 cm-1 range. Spectra are represented in wavelength (cm-1) versus transmittance (% T).

Example 1: Multifunctional Particle 1A

Aqueous solution is made by adding 50.0 g of hydroxypropyl methylcellulose (Dow) to 450 g of water at 24° C. to make an approximately 10 wt. % solution.

8.6 g citric acid and 4.3 g sodium hypophosphite monohydrate (Aldrich) are added to the hydroxypropyl methylcellulose solution.

The mixture is agitated at 600 RPM using a RW20 digital mixer with a turbine, 4-pitched blade impeller 2 inches in diameter, for 60 minutes.

3.6 g lecithin is added to 34.2 g sunflower oil and mixed at 45° C. to disperse lecithin (Cargill).

With the aqueous solution under homogenization of 24,000 RPM, the oil and lecithin mixture is added near the homogenizer wand.

The emulsion formed is agitated for an additional 5 minutes at 24,000 RPM.

Upon achieving an oil droplet median volume average diameter of less than 5 microns, 104.3 g 30 wt % aqueous solution of colloidal silica (Grace) is added to the emulsion. After mixing for 5 minutes, the emulsion is pumped to a spray drying tower and atomized using a centrifugal atomizer with co-current airflow for drying. The inlet air temperature is set at 205-210° C., the exit air temperature is stabilized at 98-103° C. Dried particles of the HPMC encapsulated oil are collected from the cyclone.

Approximately 0.1 grams of hydrophobic fumed silica (Evonik) flow agent is added to the 9.9 grams of spray-dried powder. The powder is shaken to mix for 1 minute or until a free-flowing powder is achieved. Gentle mixing in a rotary mixer, drum mixer, blender, or similar dry blending unit operation can be used to sufficiently mix the flow aid with the spray dried powder. The powder is cured in an oven at 110° C. for 20 minutes, then at 150° C. for 20 minutes.

Example 2. Multifunctional Particle 1A/S (Wax)

Aqueous solution is made by adding 50.0 g of hydroxypropyl methylcellulose (Dow) to 450 g of water at 24° C. to make an approximately 10 wt. % solution.

8.6 g citric acid and 4.3 g sodium hypophosphite monohydrate (Aldrich) are added to the hydroxypropyl methylcellulose solution.

The mixture is agitated at 600 RPM using a RW20 digital mixer with a turbine, 4-pitched blade impeller 2 inches in diameter, for 60 minutes.

3.6 g lecithin and 4.9 g soya wax are added to 29.4 g sunflower oil and mixed at 55° C. to disperse lecithin (Cargill).

With the aqueous solution under homogenization of 24,000 RPM, the oil, wax, and lecithin mixture is added near the homogenizer wand.

The emulsion formed is agitated for an additional 5 minutes at 24,000 RPM.

Upon achieving an oil droplet median volume average diameter of less than 5 microns, 104.3 g 30 wt % aqueous solution of colloidal silica (Grace) is added to the emulsion. After mixing for 5 minutes, the emulsion is pumped to a spray drying tower and atomized using a centrifugal atomizer with co-current airflow for drying. The inlet air temperature is set at 205-210° C., the exit air temperature is stabilized at 98-103° C. Dried particles of the HPMC encapsulated oil are collected from the cyclone.

Approximately 0.1 grams of hydrophobic fumed silica (Evonik) flow agent is added to the 9.9 grams of spray-dried powder. The powder is shaken to mix for 1 minute or until a free-flowing powder is achieved. Gentle mixing in a rotary mixer, drum mixer, blender, or similar dry blending unit operation can be used to sufficiently mix the flow aid with the spray dried powder. The powder is cured in an oven at 110° C. for 20 minutes, then at 150° C. for 20 minutes.

Example 3. Multifunctional Particle 1A/S/PAA (Wax and Degradation Enhancer)

Aqueous solution is made by adding 50.0 g of hydroxypropyl methylcellulose (Dow) to 450 g of water at 24° C. to make an approximately 10 wt. % solution.

8.6 g citric acid and 4.3 g sodium hypophosphite monohydrate (Aldrich) are added to the hydroxypropyl methylcellulose solution.

The mixture is agitated at 600 RPM using a RW20 digital mixer with a turbine, 4-pitched blade impeller 2 inches in diameter, for 60 minutes.

3.6 g lecithin, 3.8 g soya wax, and 3.7 g poly(acrylic acid) are added to 22.9 g sunflower oil and mixed at 55° C. to disperse lecithin (Cargill).

With the aqueous solution under homogenization of 24,000 RPM, the oil, wax, poly(acrylic acid), and lecithin mixture is added near the homogenizer wand.

The emulsion formed is agitated for an additional 5 minutes at 24,000 RPM.

Upon achieving an oil droplet median volume average diameter of less than 5 microns, 104.3 g 30 wt % aqueous solution of colloidal silica (Grace) is added to the emulsion. After mixing for 5 minutes, the emulsion is pumped to a spray drying tower and atomized using a centrifugal atomizer with co-current airflow for drying. The inlet air temperature is set at 205-210° C., the exit air temperature is stabilized at 98-103° C. Dried particles of the HPMC encapsulated oil are collected from the cyclone.

Approximately 0.1 grams of hydrophobic fumed silica (Evonik) flow agent is added to the 9.9 grams of spray-dried powder. The powder is shaken to mix for 1 minute or until a free-flowing powder is achieved. Gentle mixing in a rotary mixer, drum mixer, blender, or similar dry blending unit operation can be used to sufficiently mix the flow aid with the spray dried powder. The powder is cured in an oven at 110° C. for 20 minutes, then at 150° C. for 20 minutes.

Example 4. Multifunctional Particle 1A/S/UA (Degradation Enhancer)

Aqueous solution is made by adding 50.0 g of hydroxypropyl methylcellulose (Dow) to 450 g of water at 24° C. to make an approximately 10 wt. % solution.

8.6 g citric acid and 4.3 g sodium hypophosphite monohydrate (Aldrich) are added to the hydroxypropyl methylcellulose solution.

The mixture is agitated at 600 RPM using a RW20 digital mixer with a turbine, 4-pitched blade impeller 2 inches in diameter, for 60 minutes.

3.6 g lecithin, 3.8 g soya wax, and 3.7 g uric acid are added to 22.9 g sunflower oil and mixed at 55° C. to disperse lecithin (Cargill).

With the aqueous solution under homogenization of 24,000 RPM, the oil, wax, uric acid, and lecithin mixture is added near the homogenizer wand.

The emulsion formed is agitated for an additional 5 minutes at 24,000 RPM. Upon achieving an oil droplet median volume average diameter of less than 5 microns, 104.3 g 30 wt % aqueous solution of colloidal silica (Grace) is added to the emulsion. After mixing for 5 minutes, the emulsion is pumped to a spray drying tower and atomized using a centrifugal atomizer with co-current airflow for drying. The inlet air temperature is set at 205-210° C., the exit air temperature is stabilized at 98-103° C. Dried particles of the HPMC encapsulated oil are collected from the cyclone.

Approximately 0.1 grams of hydrophobic fumed silica (Evonik) flow agent is added to the 9.9 grams of spray-dried powder. The powder is shaken to mix for 1 minute or until a free-flowing powder is achieved. Gentle mixing in a rotary mixer, drum mixer, blender, or similar dry blending unit operation can be used to sufficiently mix the flow aid with the spray dried powder. The powder is cured in an oven at 110° C. for 20 minutes, then at 150° C. for 20 minutes.

Example 5. Multifunctional Particle 1 (Shell Only)

Aqueous solution is made by adding 50.0 g of hydroxypropyl methylcellulose (Dow) to 450 g of water at 24° C. to make an approximately 10 wt. % solution.

8.6 g citric acid and 4.3 g sodium hypophosphite monohydrate (Aldrich) are added to the hydroxypropyl methylcellulose solution.

The mixture is agitated at 600 RPM using a RW20 digital mixer with a turbine, 4-pitched blade impeller 2 inches in diameter, for 60 minutes.

After mixing for 5 minutes, the solution is pumped to a spray drying tower and atomized using a centrifugal atomizer with co-current airflow for drying. The inlet air temperature is set at 205-210° C., the exit air temperature is stabilized at 98-103° C. Dried particles of the HPMC encapsulated oil are collected from the cyclone.

Approximately 0.1 grams of hydrophobic fumed silica (Evonik) flow agent is added to the 9.9 grams of spray-dried powder. The powder is shaken to mix for 1 minute or until a free-flowing powder is achieved. Gentle mixing in a rotary mixer, drum mixer, blender, or similar dry blending unit operation can be used to sufficiently mix the flow aid with the spray dried powder. The powder is cured in an oven at 110° C. for 20 minutes, then at 150° C. for 20 minutes.

Example 6A. PLA Resin Filament (No Multifunctional Particle)—Filament 40-0

PLA composite filament is extruded to observe the particle survival during extrusion and dispersion in the matrix PLA, as well as test mechanical properties of the composite. Dried particles are prepared for melt compounding by sieving through a 44 micron wire mesh sieve and dried at 80° C. overnight. NatureWorks Ingeo Biopolymer 4043D grade poly(lactic acid) is used as the matrix polymer. No particles are added to the polymer matrix.

1.75 mm diameter 3D printer filament is extruded from NatureWorks Ingeo 4043D PLA with a ¾ inch single-screw Brabender Processing Plasti-Corder PL 2000 extruder fitted with a single-stage mixing screw of L/D 20:1 to a diameter of approximately 1.75 mm. A nominal nozzle temperature of 150° C., barrel temperature of 160° C., and die temperature of 160° C., and a screw speed of 28 rpm are used. The filament is water cooled with water bath held at room temperature.

Example 6B. PLA Resin Filament with Only Shell Material—Filament 4-1-3

PLA composite filament is extruded to observe the particle survival during extrusion and dispersion in the matrix PLA, as well as test mechanical properties of the composite. Dried particles are prepared for melt compounding by sieving through a 44 micron wire mesh sieve and dried at 80° C. overnight. NatureWorks Ingeo Biopolymer 4043D grade poly(lactic acid) is used as the matrix polymer. Particles as described in Example 5, shell material particle, are mixed into the dried PLA before melt compounding at 3 equivalent wt %

Natural Poly(lactic acid) (PLA) 1.75 mm diameter 3D printer filament is extruded from NatureWorks Ingeo 4043D PLA with a ¾ inch single-screw Brabender Processing Plasti-Corder PL 2000 extruder fitted with a single-stage mixing screw of L/D 20:1 to a diameter of approximately 1.75 mm. A nominal nozzle temperature of 150° C., barrel temperature of 160° C., and die temperature of 160° C., and a screw speed of 28 rpm are used. The filament was water cooled with water bath held at room temperature.

Example 6C. PLA Resin Filament with Only Core Material (High Plasticization)—Filament 4-A-3

PLA composite filament is extruded to observe the particle survival during extrusion and dispersion in the matrix PLA, as well as test mechanical properties of the composite. Dried particles are prepared for melt compounding by sieving through a 44 micron wire mesh sieve and dried at 80° C. overnight. NatureWorks Ingeo Biopolymer 4043D grade poly(lactic acid) is used as the matrix polymer. The core natural oil is mixed directly with the dried PLA before melt compounding at a mass equivalent to 3 wt %.

Natural Poly(lactic acid) (PLA) 1.75 mm diameter 3D printer filament is extruded from NatureWorks Ingeo 4043D PLA with a ¾ inch single-screw Brabender Processing Plasti-Corder PL 2000 extruder fitted with a single-stage mixing screw of L/D 20:1 to a diameter of approximately 1.75 mm. A nominal nozzle temperature of 150° C., barrel temperature of 160° C., and die temperature of 160° C., and a screw speed of 28 rpm are used. The filament was water cooled with water bath held at room temperature.

Example 6D. PLA Composite with Multifunctional Particle—Filament 4-1A-3

PLA composite filament is extruded to observe the particle survival during extrusion and dispersion in the matrix PLA, as well as test mechanical properties of the composite. Dried particles are prepared for melt compounding by sieving through a 44 micron wire mesh sieve and dried at 80° C. overnight. NatureWorks Ingeo Biopolymer 4043D grade poly(lactic acid) is used as the matrix polymer. Particles 1A as described in Example 1 are mixed into the dried PLA before melt compounding at 3 wt %.

Natural Poly(lactic acid) (PLA) 1.75 mm diameter 3D printer filament is extruded from NatureWorks Ingeo 4043D PLA with a ¾ inch single-screw Brabender Processing Plasti-Corder PL 2000 extruder fitted with a single-stage mixing screw of L/D 20:1 to a diameter of approximately 1.75 mm. A nominal nozzle temperature of 150° C., barrel temperature of 160° C., and die temperature of 160° C., and a screw speed of 28 rpm are used. The filament was water cooled with water bath held at room temperature.

Example 6E. PLA Composite with Multifunctional Particle—Filament 4-1A/S/PAA-6

PLA composite filament is extruded to observe the particle survival during extrusion and dispersion in the matrix PLA, as well as test mechanical properties of the composite. Dried particles are prepared for melt compounding by sieving through a 44 micron wire mesh sieve and dried at 80° C. overnight. NatureWorks Ingeo Biopolymer 4043D grade poly(lactic acid) is used as the matrix polymer. Particles 1A as described in Example 1 are mixed into the dried PLA before melt compounding at 6 wt %.

Natural Poly(lactic acid) (PLA) 1.75 mm diameter 3D printer filament is extruded from NatureWorks Ingeo 4043D PLA with a ¾ inch single-screw Brabender Processing Plasti-Corder PL 2000 extruder fitted with a single-stage mixing screw of L/D 20:1 to a diameter of approximately 1.75 mm. A nominal nozzle temperature of 150° C., barrel temperature of 160° C., and die temperature of 160° C., and a screw speed of 28 rpm are used. The filament was water cooled with water bath held at room temperature.

Example 7. Multifunctional Particle with Low Free Oil

Aqueous solution is made by adding 50.0 g of hydroxypropyl methylcellulose (Dow) to 450 g of water at 24° C. to make an approximately 10 wt. % solution.

8.6 g citric acid and 4.3 g sodium hypophosphite monohydrate (Aldrich) are added to the hydroxypropyl methylcellulose solution.

The mixture is agitated at 600 RPM using a RW20 digital mixer with a turbine, 4-pitched blade impeller 2 inches in diameter, for 60 minutes.

4.9 g lecithin is added to 34.2 g fragrance oil and mixed at 45° C. to disperse lecithin (Cargill).

With the aqueous solution under homogenization of 24,000 RPM, the oil and lecithin mixture is added near the homogenizer wand.

The emulsion formed is agitated for an additional 5 minutes at 24,000 RPM.

Upon achieving an oil droplet median volume average diameter of less than 5 microns, 104.3 g 30 wt % aqueous solution of colloidal silica (Grace) is added to the emulsion. After mixing for 5 minutes, the emulsion is pumped to a spray drying tower and atomized using a centrifugal atomizer with co-current airflow for drying. The inlet air temperature is set at 205-210° C., the exit air temperature is stabilized at 98-103° C. Dried particles of the HPMC encapsulated oil are collected from the cyclone.

Approximately 0.1 grams of hydrophobic fumed silica (Evonik) flow agent is added to the 9.9 grams of spray-dried powder. The powder is shaken to mix for 1 minute or until a free-flowing powder is achieved. Gentle mixing in a rotary mixer, drum mixer, blender, or similar dry blending unit operation can be used to sufficiently mix the flow aid with the spray dried powder. The powder is cured in an oven at 110° C. for 20 minutes, then at 150° C. for 20 minutes. The particles must withstand simultaneous shear and thermal stresses in the extruder as well as during printing without releasing their payloads. It is assumed that free or easily extractable oil on the surface of the particles acts as a plasticizer in the matrix. To gain information about the free oil released due to thermal stress and the barrier properties of the shell under thermal stress, free oil testing was performed on the particles to determine the likely extent of release under conditions simulating extrusion. 210° C. was chosen to simulate the higher temperature condition of fused filament fabrication, rather than extrusion of the filament which is performed at 165° C. Only the effect of heating, without the effect of concurrent shear, was measured in this manner.

To perform the free oil test, uncured and cured versions of Example 1 were heated to 210° C. in a nitrogen gas environment for 10 min. GC/MS hexane extraction method was used to analyze the free oil.

The free oil results of the spray-dried particles given in Table 4 below indicate that the free oil percentage of the total oil in the spray dried uncured particles is somewhat high (8%-14%). This percentage of free oil is substantially reduced upon curing to between 0%-3% of the initial oil content of the particle. The cured samples heated to 210° C. lost approximately 3% of the perfume oil during the heating process, which translates to less than 0.1 wt % of the total filament. The low value of free oil indicates that a very low percentage of oil is leaking into the matrix during 3D printing, and the effect of this amount of oil in the matrix as a plasticizer is likely to be very small.

TABLE 4

| % Perfume Loading | % Free Oil | Sample Description |
|---|---|---|
| 28.00% | 13.88% | Particle 1A Formula, Uncured |
| 28.00% | 8.22% | Particle 1A, Low Mw, Uncured |
| 28.00% | 2.97% | Particle 1A Formula, Cured |
| 28.00% | 0.01% | Particle 1A Low Mw, Cured |
| 28.00% | 2.36% | Particle 1A Formula, Cured Nitrogen Environment 210° C., 10 minutes |
| 28.00% | Below detection limit | Particle 1A, Low Mw, Cured Nitrogen Environment, 210° C. 10 minutes |

Giita, et al. [V.S. Giita Silverajah, N. A. Ibrahim, N. Zainuddin, W. M. Z. Wan Yunus, H. A. Hassan, Mechanical, thermal and morphological properties of poly(lactic acid)/epoxidized palm olein blend, Molecules. 17 (2012) 11729-11747. doi:10.3390/molecules171011729] tested an epoxidized palm olein as a plasticizer for PLA, and found that tensile strength and modulus increased at 1 wt % loading, and began to decrease at 2 wt %.

Knowledge of the amount of oil can give some indication of the reason for changes in mechanical properties upon addition of particles. In this case, excess free oil is ruled out as being available to act as a plasticizer in the matrix and affecting the mechanical properties.

Example 8. Tunable Properties

Figure 4:
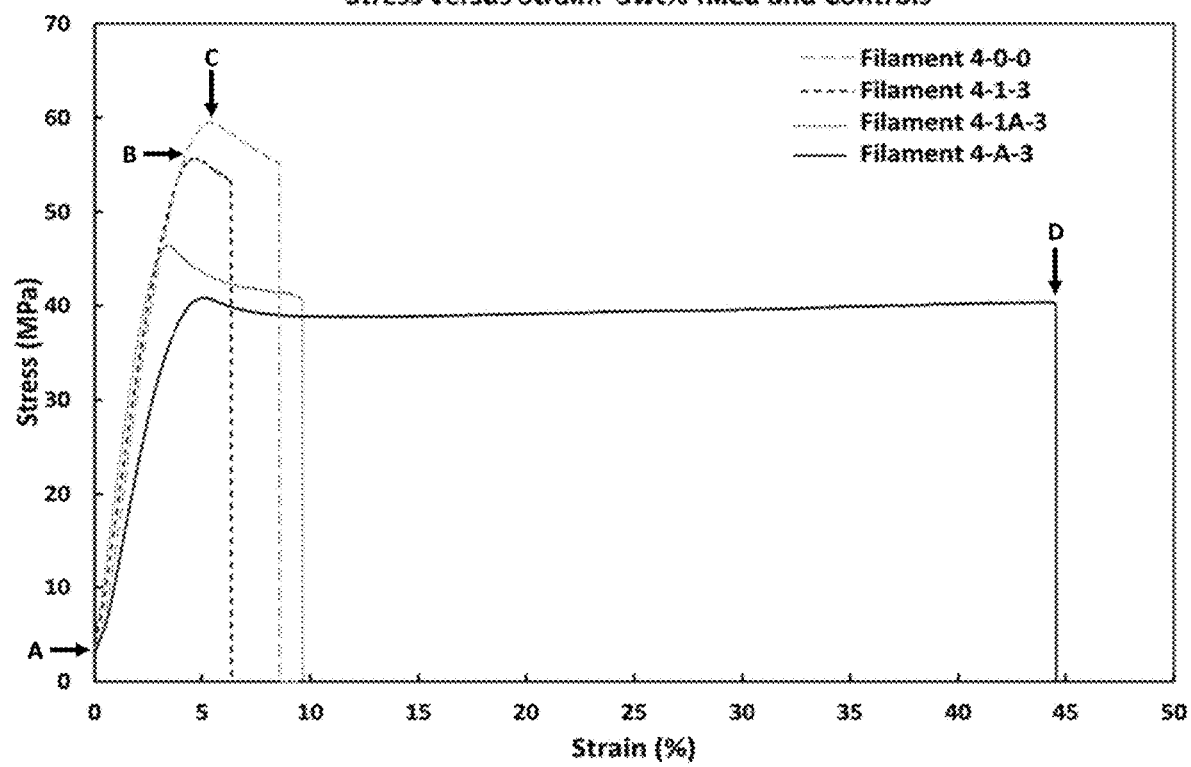
FIG. 4 shows the stress-strain curves from mechanical testing of polylactic acid composite prepared in Example 8. PLA filament containing the core material only and shell material only at the equivalent of 3 wt % of the complete additive particle are plotted against neat PLA and PLA with an additive particle loading at 3 wt %. The Young's modulus is the calculated slope of the linear portion of the stress-strain curve, indicated on the curve of Filament 40-0 as the region approximately indicated between Point A and Point B. The yield strength is taken as the maximum value of each stress-strain curve, indicated as Point C on the curve of Filament 40-0. The percent elongation is calculated by dividing the difference in gage length at failure (Point D, Filament 4-A-3) by the initial gage length (Point A) and multiplying by 100. The filament containing free core material only showed the greatest increase in elongation compared to the neat PLA filament, for an increase of 236%. However, while the difference in yield strength for the 3 wt % loading level between encapsulated oil and free oil is minimal, the loss in Young's modulus is substantial.

The formula of the particle can affect the properties of the composite material. The minimum values for stiffness were Filament 4-1A-6 ((poly(lactic acid) resin 4043D, Particle 1A of Example 1, at 6 wt % loading in the filament) and Filament 4-A-3 ((poly(lactic acid) resin 4043D, core material of Example 1, at 3 wt % equivalent loading in the filament). For strength the minimum values were from Filament 4-1A/S-6 ((poly(lactic acid) resin 4043D, Particle 1A/S of Example 2, at 6 wt % loading in the filament) and 4-1A-6 ((poly(lactic acid) resin 4043D, Particle 1A of Example 1, at 6 wt % loading in the filament). Filaments 4-1-3 ((poly(lactic acid) resin 4043D, Particle 1 of Example 5 at 3 equivalent wt % loading in the filament) and 4-1A-1.5 ((poly(lactic acid) resin 4043D, Particle 1A of Example 1, at 1.5 wt % loading in the filament) gave the lowest percent elongation, see FIG. 4. In summary, the highest strength and stiffness was given by particles with a polysaccharide shell, with natural oil core, core stiffener, and either uric acid with loading at 3 wt % or without uric acid at 6 wt %. The greatest elongation was given by the particle with the lowest yield strength. In between these values lie a range of properties and combinations of yield strength, modulus, and elongation.

TABLE 5

| Parameter (Average) | Filament 4-0-0 | Filament 4-1-3 | Filament 4-A-3 | Filament 4-1A-3 |
|---|---|---|---|---|
| Young's Modulus (GPA) | 1.60 | 1.53 | 1.36 | 1.66 |
| Yield Strength (MPa) | 58.2 | 52.7 | 44.5 | 45.1 |
| % Elongation | 9.34 | 6.1 | 31.4 | 10.2 |

Example 9. Mechanical Property Characterization of the Polylactic Acid Composite (Elongation, Yield Strength, Modulus)

Figure 5:
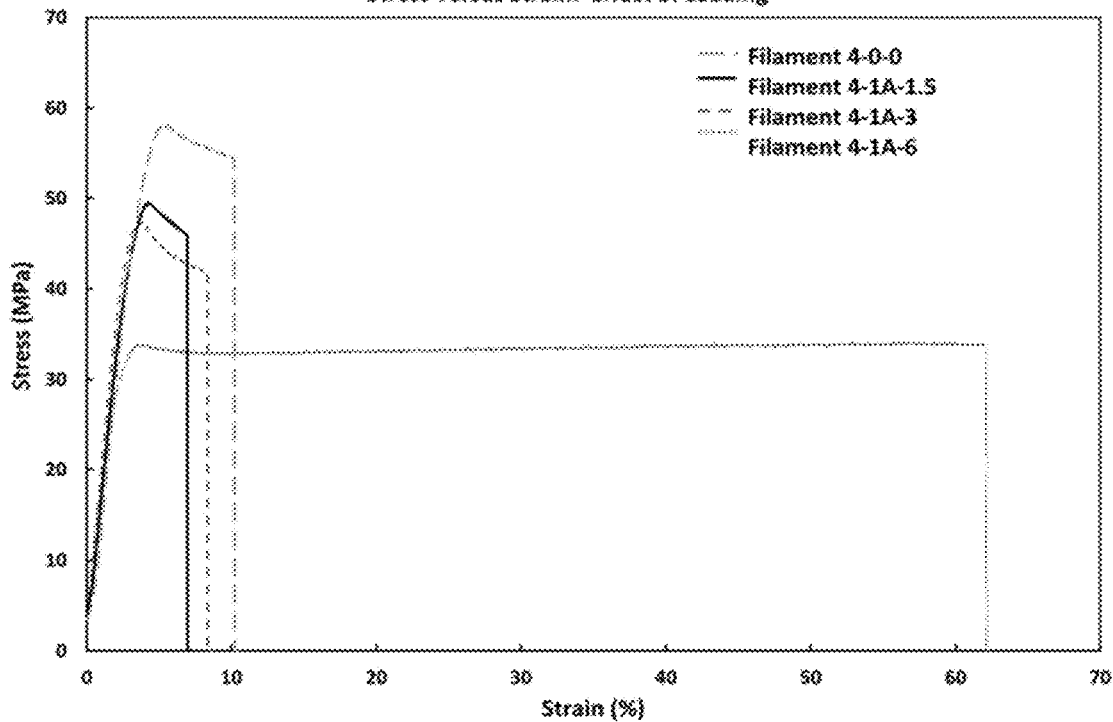
FIG. 5 shows the stress-strain curves from mechanical testing of polylactic acid composite prepared in Example 9. The multifunctional additive particle is added at levels 1.5 wt %, 3 wt %, and 6 wt % into 4043D PLA and plotted against filament made from neat 4043D powder. By comparison of levels of loading with the same particle, it is possible to observe the effect of additive concentration on the composite mechanical properties. The increased loading of particles decreases yield strength while increasing elongation, which is typical of rubber toughening.

Tensile testing was used to screen the experimental particles that were fabricated by their effect on the filament properties. The testing was performed directly on the filament and the quantities monitored were yield strength, Young's modulus, and elongation at break. Screening for tensile strength and tensile toughness was performed using a modified ASTM D638-14 (Standard Test Methods for Tensile Properties of Plastics) on a screw-driven Instron 5567 outfitted with rope grips, as specified in Section 3.2. Instron Bluehill 3 software used to collect and export data. FIG. 5 shows the stress-strain curves, and Table 6 below provides the mechanical testing results. The Young's modulus is the calculated slope of the linear portion of the stress-strain curve, indicated on FIG. 4 of curve (Filament 40-0) as the region approximately indicated between Point A and Point B. The yield strength is taken as the maximum value of the stress-strain curve, indicated on FIG. 4 as Point C. The percent elongation is calculated by dividing the difference in gage length at failure (Point D, Filament 4-A-3) by the initial gage length (Point A) and multiplying by 100.

TABLE 6

| Parameter (Average) | Filament 4-0-0 | Filament 4-1A-1.5 | Filament 4-1A-3 | Filament 4-1A-6 |
|---|---|---|---|---|
| Young's Modulus (GPA) | 1.60 | 1.58 | 1.66 | 1.35 |
| Yield Strength (MPa) | 58.2 | 51.8 | 45.1 | 35.8 |
| Elongation at Break (%) | 9.34 | 8.73 | 10.2 | 47.8 |

Example 10. Biodegradability Rate Example

The compostability testing was based on a modified ASTM D5338 Soil Contact Test. The compost testing was observed each week for the presence of microbial colonies and for changes in the appearance of the samples. FIGS. 6A, 6B and 6C below show images of modified ASTM 5338 composting setup during testing. The filaments are embedded in a jar filled with compost. Microbial colonies develop begin to develop at Week 3, localized around the filaments. The microbial colonies began to appear at Week 3 (21 days) for each sample. This aligns with the general stages of composting, wherein the mesophilic phase involves growth of the microorganisms and assimilation of material. In this case, the lag is likely due to hydrolysis of the material under test, which provides more available material for microbes to digest and assimilate. After 8 weeks, all filaments become encased in microbial colonies along the length of the filament embedded in soil, see FIGS. 6A, 6B and 6C.

The visible colonies that appear at Week 3 and continue through Week 8 most likely reflect the thermophilic phase of composting, in which the decomposition is carried out by thermophilic bacteria, actinobacteria, and fungi. By Week 8, the microbial colonies visibly shrink and filament is more fragmented and difficult to recover, which likely reflects the beginning of the cooling (second mesophilic) phase of composting, where the available food sources for the microbes become scarce and mesophiles begin to feed on lower-energy compounds such as cellulose or starch. The microbes available in these phases are likely skewed by the constant elevated temperature of the simulated test, but the phases may progress in the same way based on the nutrient sources available. FIG. 7 shows a 24% improvement in the composting rate with additives vs. without.

Example 11. Injection-Molded Product

PLA pellets of NatureWorks Ingeo Grade 4043D are dried at 80° C. for 3 hours and injection molded on a Nissai injection molding machine with the nozzle set to 202° C., barrel at 210° C., mold base at 28° C., and a cool time of 40 seconds.

While the invention has been described in detail and with reference to specific examples thereof, it will be apparent to one skilled in the art that various changes and modifications can be made therein without departing from the spirit and scope thereof.

What is claimed is:
1. A biodegradable resin composite material comprising: a biodegradable polymer resin; and multifunctional particles, wherein: (a) the multifunctional particles comprise 10-70 wt. % of a hydrophobic active ingredient, 21-72 wt. % of a polysaccharide, 3.80-20 wt. % of a crosslinking agent, 1.00-6 wt. % of a catalyst, 0.10-5 wt. % of a silica flow aid, optionally 0.10-5 wt. % of a desiccant, optionally 0.20-20 wt. % of an emulsifier, optionally 1-10 wt. % of a degradation enhancer, and optionally 1-10 wt. % of particle dispersion aids; (b) the multifunctional particles are anhydrous; and (c) the hydrophobic active ingredient is encapsulated in a crosslinked polysaccharide matrix.

2. The biodegradable resin composite material of claim 1, wherein the biodegradable polymer resin is a polylactic acid and the biodegradable resin composite material has: (i) an elongation of 6% to 400%; (ii) a Young's modulus of 0.5-6.0 gigapascals; (iii) a notched Izod impact strength of 16-650 J/m as measured by ASTM D256 or 2-150 kJ/m$^2$ as measured by ISO 180; and (iv) a yield strength of 25-120 Megapascals.

3. The biodegradable resin composite material of claim 2, having a rate of biodegradability that is at least 10% higher than the polylactic acid resin alone.

4. The biodegradable resin composite material of claim 1, further comprising at least one supplemental additive comprising at least one material selected from the group consisting of nanoclays, lignin, cellulose, triggered release technology, charcoal, talc, distillers dried grains with solubles, calcium carbonate and polyhydroxyalkanoate.

5. The biodegradable resin composite material of claim 1, wherein the hydrophobic active ingredient is a member selected from the group consisting of a flavorant, a fragrance, a chromogen, a dye, an essential oil, a sweetener, a pigment, an active pharmaceutical ingredient, a moldicide, a herbicide, a fertilizer, a phase change material, an adhesive, a vitamin oil, a vegetable oil, a triglyceride and a hydrocarbon.

6. The biodegradable resin composite material of claim 1, wherein the polysaccharide is a member selected from the group consisting of cellulose, cellulose derivatives, natural starches, natural gums and modified starches.

7. The biodegradable resin composite material of claim 1, wherein the crosslinking agent is a member selected from the group consisting of dimethyldihydroxy urea, dimethyloldihydroxyethylene urea, dimethylol urea, dihydroxyethylene urea, dimethylolethylene urea, dimethyldihydroxyethylene urea, citric acid, tartaric acid, malic acid, succinic acid, glutaric acid, citraconic acid, itaconic acid, tartrate monosuccinic acid, maleic acid, poly(acrylic acid), poly(methacrylic acid), poly(maleic acid), poly(methylvinylether-co-maleate) copolymer, copolymers of acrylic acid and copolymers of maleic acid.

8. The biodegradable resin composite material of claim 1, wherein the catalyst is a member selected from the group consisting of ammonium chloride, ammonium sulfate, aluminum chloride, magnesium chloride, magnesium nitrate and sodium hypophosphite.

9. The biodegradable resin composite material of claim 1, wherein the silica flow aid is a member selected from the group consisting of fumed silica, precipitated silica, calcium silicate, aluminosilicate, and combinations thereof.

10. The biodegradable resin composite material of claim 1, which includes the emulsifier, and the emulsifier is a member selected from the group consisting of nonionic emulsifiers, phospholipids, and combinations thereof.

11. The biodegradable resin composite material of claim 1, which includes the degradation enhancer, and the degradation enhancer is a member selected from the group consisting of microbial growth enhancers, fertilizers, lipases, esterases, proteases, amylases, cellulases, materials that contain at least one carboxylic acid moiety and combinations thereof.

12. The biodegradable resin composite material of claim 1, wherein the multifunctional particles have a diameter from 0.035 microns to less than 100 microns.

13. The biodegradable resin composite material of claim 1, which is in a form of a packaging product, a textile, an eating utensil, a cup, a plate, a card, a carton, an electrical component, an electrical device, an appliance, a medical product, a hygiene product, a landscaping product, an agricultural product, a solid fabric enhancer, a solid shampoo, a solid antiperspirant, a solid deodorant, a solid detergent, a solid hard surface cleaner, a diaper, a controlled release fertilizer, a controlled release insecticide, a controlled release dye, a film, or articles comprising nanocomposites.

14. The biodegradable resin composite material of claim 1, wherein the hydrophobic active ingredient comprises a mixture of a hydrophobic active and a material selected from the group consisting of plant waxes, animal waxes, petroleum based waxes, synthetic waxes, mineral waxes, brominated oils, hydrophobically modified inorganic particles, nonionic emulsifiers and oil thickening agents.

15. A method for preparing the biodegradable resin composite material of claim 1, said method comprising:
    mixing the hydrophobic active ingredient and optionally the degradation enhancer to provide a homogeneous solution;
    mixing the homogeneous solution with a polysaccharide solution comprising a polysaccharide, a crosslinking agent, a catalyst, an optional emulsifier and water to provide an emulsion;
    agitating the emulsion to provide a modified emulsion containing hydrophobic active ingredient droplets with a volume average diameter of less than 5 microns;
    crosslinking the hydrophobic active ingredient droplets in the modified emulsion to form either a core/shell structure or a matrix structure in a further modified emulsion;
    dewatering the further modified emulsion to provide a powder;
    adding the silica flow aid to the powder to provide a modified powder;
    drying the modified powder to provide the multifunctional particles;
    drying a polylactic acid resin;
    introducing the polylactic acid resin into a vessel at a temperature effective to provide melted resin; and
    adding the multifunctional particles to the melted resin under shear to provide the biodegradable resin composite material.

16. The method of claim 15, further comprising incorporating additives into the melted resin, and the biodegradable resin composite material is a homogeneous mixture of the polylactic acid resin, the multifunctional particles and the additives.

* * * * *